US00RE45720E

(19) United States
(12) Reissued Patent
Chaplin et al.

(10) Patent Number: US RE45,720 E
(45) Date of Reissued Patent: Oct. 6, 2015

(54) FUNCTIONALIZED STILBENE DERIVATIVES AS IMPROVED VASCULAR TARGETING AGENTS

(71) Applicants: OXiGENE, Inc., South San Francisco, CA (US); Baylor University, Waco, TX (US)

(72) Inventors: David J. Chaplin, Watlington (GB); Charles Manly Garner, III, McGregor, TX (US); Robert Ronald Kane, Waco, TX (US); Kevin G. Pinney, Woodway, TX (US); Joseph Anthony Prezioso, Boston, MA (US); Klaus Edvardsen, Klampenborg (DK)

(73) Assignees: OXiGENE, Inc., South San Francisco, CA (US); Baylor University, Waco, TX (US)

(21) Appl. No.: 14/180,209

(22) Filed: Feb. 13, 2014

Related U.S. Patent Documents

Reissue of:
(64) Patent No.: 6,919,324
Issued: Jul. 19, 2005
Appl. No.: 10/281,528
Filed: Oct. 28, 2002

U.S. Applications:
(60) Provisional application No. 60/337,348, filed on Oct. 26, 2001.

(51) Int. Cl.

| | |
|---|---|
| ***C07C 207/00*** | (2006.01) |
| ***C07C 207/04*** | (2006.01) |
| ***C07C 205/37*** | (2006.01) |
| ***C07C 205/00*** | (2006.01) |
| ***C07C 217/00*** | (2006.01) |
| ***C07C 237/00*** | (2006.01) |
| ***C07C 217/84*** | (2006.01) |
| ***C07C 237/04*** | (2006.01) |
| ***C07C 43/00*** | (2006.01) |
| ***C07C 45/63*** | (2006.01) |
| ***C07C 43/23*** | (2006.01) |
| ***C07F 9/00*** | (2006.01) |
| ***C07C 9/12*** | (2006.01) |
| ***C07C 47/575*** | (2006.01) |
| *C07F 9/12* | (2006.01) |

(52) U.S. Cl.
CPC . *C07C 43/23* (2013.01); *C07C 9/12* (2013.01); *C07C 45/63* (2013.01); *C07C 47/575* (2013.01); *C07C 205/37* (2013.01); *C07C 207/04* (2013.01); *C07C 217/84* (2013.01); *C07C 237/04* (2013.01)

(58) Field of Classification Search
CPC .... C07C 43/23; C07C 205/37; C07C 217/84; C07C 237/04; C07C 47/575; C07C 45/63; C07F 9/12
USPC ..... 514/114; 558/70, 155, 166, 169
See application file for complete search history.

(56) References Cited

U.S. PATENT DOCUMENTS

| | | | | |
|---|---|---|---|---|
| 5,430,062 | A | 7/1995 | Cushman et al. | |
| 5,525,632 | A | 6/1996 | Obsumi et al. | |
| 5,561,122 | A * | 10/1996 | Pettit | 514/130 |
| 5,886,025 | A | 3/1999 | Pinney | |
| 6,214,886 | B1 * | 4/2001 | Potter et al. | 514/685 |
| 6,346,550 | B2 * | 2/2002 | Potter et al. | 514/685 |
| 6,423,753 | B1 | 7/2002 | Dougherty | |
| 6,479,512 | B1 * | 11/2002 | Fraley et al. | 514/312 |
| 6,538,038 | B1 * | 3/2003 | Pero et al. | 514/731 |
| 6,919,324 | B2 | 7/2005 | Chaplin et al. | |
| 7,078,552 | B2 | 7/2006 | Pettit et al. | |
| 7,220,784 | B2 | 5/2007 | Hadfield et al. | |

FOREIGN PATENT DOCUMENTS

| | | |
|---|---|---|
| WO | 92/16486 | 10/1992 |
| WO | 99/35150 | 7/1999 |
| WO | WO 9935150 A1 * | 7/1999 |
| WO | 00/40529 | 7/2000 |
| WO | 01/81355 | 11/2001 |
| WO | 02/14329 | 2/2002 |
| WO | 02/49994 | 6/2002 |
| WO | 02/50007 | 6/2002 |

OTHER PUBLICATIONS

Bedford et al., "Synthesis of Water-Soluble Prodrugs of the Cytotoxic Agent Combretastatin A4." Bioorganic & Medicinal Chemistry Letters, 1996, vol. 6, No. 2, pp. 157-160.

Cushman et al., "Synthesis and Evaluation of Analogues of (Z)-1-(4-Methoxyphenyl)-2-(3,4,5-trimethoxyphenyl) ethene as Potential Cytotoxic and Antimitotic Agents." J. Med. Chem. , 1992, vol. 35, pp. 2293-2306.

Lin et al., "Interactions of Tubulin with Potent Natural and Synthetic Analogs of the Antimitotic Agent Combretastatin: a Structure-Activity Study." Molecular Pharmacology, 1988, vol. 34, pp. 200-208.

Ohsumi, et al., "Novel combretastatin analogues effective against murine solid tumors: design and structure-activity relationships." J. Med. Chem., 1998, vol. 41, pp. 3022-3032.

Orsini et al., "Synthesis of biologically active polyphenolic glycosides (combretastatin and resveratrol series)." Carbohydrate Research, 1997, vol. 301, pp. 95-109.

(Continued)

*Primary Examiner* — Evelyn Huang
(74) *Attorney, Agent, or Firm* — Shay Glenn LLP

(57) ABSTRACT

Novel stilbenoid compounds and their prodrug forms are disclosed, which serve as potent vascular targeting agents useful for the treatment of solid tumor cancers and other diseases associated with unwanted neovascularization. The novel stilbenoid compounds are tubulin-binding stilbenoid analogs structurally related to combretastatin A-1 and combretastatin A-4. The prodrug forms serve as potent vascular targeting agents (VTAs) useful for the treatment of solid tumor cancers and diseases associated with retinal neovascularization.

5 Claims, 3 Drawing Sheets

(56) References Cited

OTHER PUBLICATIONS

Figure 1:
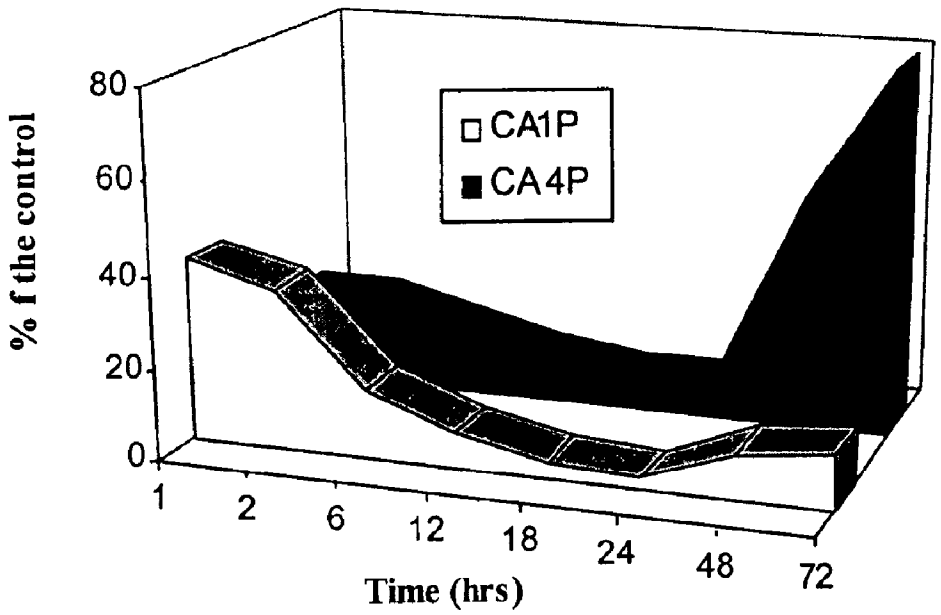

Pettit et al., "Antineoplastic agents 322. Synthesis of combretastatin A-4 prodrugs." Anti-Cancer Drug Design, 1995, vol. 10, pp. 299-309.
Pettit et al., "Antineoplastic agents 389. New syntheses of the combretastatin A-4 prodrug." Anti-Cancer Drug Design, 1998, vol. 13, pp. 183-191.
Pettit et al., "Antineoplastic Agents. 379. Synthesis of phenstatin Phosphate 1a." J. Med. Chem., 1998, vol. 41, pp. 1688-1695.
Pettit and Lippert, "Antineoplastic Agents 429. Syntheses of the combretastatin A-1 and combretastatin B-1 prodrugs." Anti-Cancer Drug Design, 2000, vol. 15, pp. 203-216.
Pettit, et al., "Antineoplastic Agents 440. Asymmetric Synthesis and Evaluation of the combretastatin A-1 SAR Probes (1S,2S)- and (1R,2R)-1,2-dihydroxy-1-(2',3'-dihydroxy-4'-methoxyphenyl)-2-(3",4",5"-trimethoxyphenyl-ethane." J. Natural Products, 2000, vol. 63, pp. 969-974.
Ueda, et al., "Novel water soluble phosphate prodrugs of Taxol possessing in vivo antitumor activity." Bioorg. Med. Chem. Letters, 1993, vol. 3, pp. 1761-1766.
Vyas, et al., "Synthesis and antitumor evaluation of water soluble taxol phosphates." Bioorg. Med. Chem. Letters, 1993, vol. 3, pp. 1357-1360.
Pettit et al.; Preparation and formulation of combretastatin A4 prodrugs and their trans-isomers for use as antitumor agents; STN International, CAPLUS Database; Accession No. 1999:451301; Document No. 131:73507; 1999 (year of pub. sufficiently earlier than effective US filing date and any foreign priority date).
Pettit et al (1999): STN International, caplus database (Columbus, Ohio); Accession No. 1999;451301.*
Cushman, et al. (1992). J Med Chem 35: 2293-2306.
Pettit, et al. (1998). J Med Chem 41: 1688-1695.
International Search Report for PCT/ US 02/34497, mailed May 2, 2003.

* cited by examiner

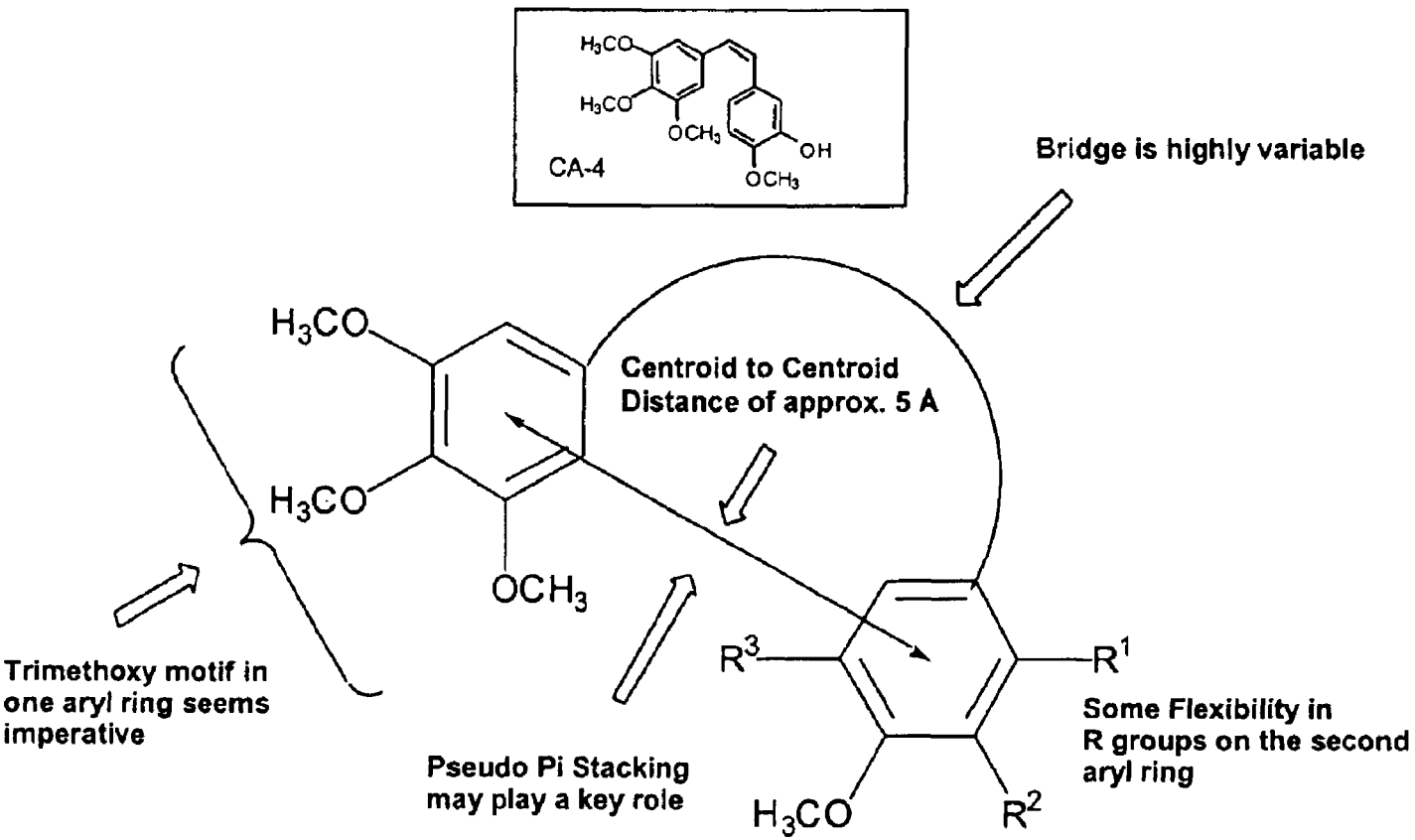
Figure 3. Salient SAR Features of Stilbenoid VTAs

FUNCTIONALIZED STILBENE DERIVATIVES AS IMPROVED VASCULAR TARGETING AGENTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED INVENTION

This application claims priority benefit under 35 U.S.C. §119(e) of U.S. Provisional Patent Application Ser. No. 60/337,348 filed on Oct. 26, 2001, the entire disclosure of which is incorporated herein by reference.

FIELD OF THE INVENTION

The present invention relates to new stilbenoid compounds and their prodrug forms, which serve as potent vascular targeting agents useful for the treatment of solid tumor cancers and other diseases associated with unwanted neovascularization.

More particularly, the present invention relates to tubulin-binding stilbenoid analogs structurally related to combretastatin A-1 and combretastatin A-4.

BACKGROUND OF INVENTION

The discovery of the natural products collectively known as the combretastatins from a willow tree (Combretum caffrum) in South Africa ushered in a new era in the development of antimitotic agents which inhibit the assembly of tubulin into microtubules. Combretastatin A-4 (CA-4) and combretastatin A-1 (CA-1), which have the structures:

CA-4

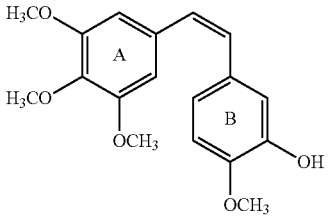

CA-1

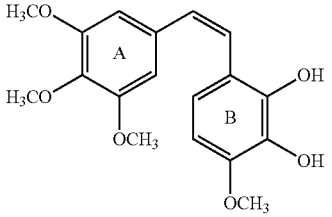

are especially potent in terms of in vitro cytotoxicity against human cancer cell lines and in their ability to inhibit the assembly of tubulin into microtubules through a direct interaction at the colchicine binding site on β-tubulin.

It is interesting and instructive to note that while both CA-4 and CA-1 are potent inhibitors of tubulin assembly and are strongly cytotoxic against human cancer cell lines (Table 1), both of these in vitro assays suggest that CA-4 is more active biologically than CA-1.

TABLE 1

In Vitro Evalutation of Combretastatins and Combretastatin Prodrugs

| | Inhibition of Tubulin Polymerization ($IC_{50}$) | MTT Cytotoxicity ($IC_{50}$) at 1 hour | MTT Cytotoxicity ($IC_{50}$) at 5 hours |
|---|---|---|---|
| CA-4 | 1-2 uM | 0.1 uM | 0.05 uM |
| CA-1 | 2-4 uM | 10 uM | 0.05 uM |
| CA-4P | >40 uM | 0.8 uM | 0.002 uM |
| CA-1P | >40 uM | 3.2 uM | 0.0046 uM |

However, when both of these analogs are converted to their corresponding prodrug forms (CA-4P and CA-1P accordingly) and evaluated in vivo in terms of tumor vascular shutdown (FIG. 1) and tumor growth delay (FIG. 2), then it is apparent that CA-1P is eight to ten-fold more active than CA-4P in SCID mice. CA4P and CA1P have structures:

CA-4P

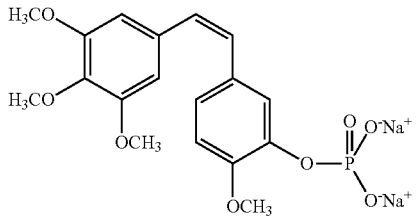

CA-1P

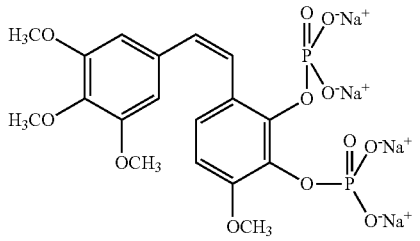

In the case of CA-1P, the most probable biological mode of action ultimately appears to be an enzymatic cleavage by non-specific alkaline phosphatase (or a related enzyme) converting CA-1P (which is not active with tubulin) to the parent CA-1 (which is active with tubulin). CA-1 inhibits the assembly of cytoskeletal tubulin into microtubules resulting in a morphological change in the endothelial cells lining the microvessels of tumors. This morphological change causes the endothelial cells to "round-up" which results in an inability of the microvessels to sustain blood flow. Blood clotting and other events ensue which ultimately result in death of the surrounding tumor tissue. Healthy tissues are, for the most part, not affected even though the compound is administered systemically. Several possibilities exist for this selectivity including (but not limited to): (a) the possibility that there is enhanced activity or expression of nonspecific alkaline phosphatase in the micro-environment of the endothelial cells lining the tumor microvessels; (b) potential differences in the tubulin itself between mature healthy cells and immature, rapidly proliferating endothelial cells in the tumor microvessels which cause enhanced disruption of the tubulin assembly/disassembly process in the tumor microenvironment; (c) tumor cells are known to have "leaky" vessels and it is possible that some of the improved tumor growth delay is due to the compound (as parent drug or prodrug) leaving the blood vessels and entering the cytosol around the tumor where it can form a "supply pool" which ultimately enters the tumor cell itself and (as the parent compound) functions as an antimitotic agent inhibiting cellular division during metaphase of the cell cycle. The enhanced (10 fold) activity in vivo of CA-1P may be due, in part, to the pharmacokinetics associated with the cleavage of both of the phosphate groups (perhaps one cleaves more rapidly than the other) and the subsequent interaction of the parent diphenol (or perhaps one, or both, of the monophenols/monophosphates) with tubulin.

It has therefore been an object of the studies which led to the present invention to demonstrate and confirm that the enhanced activity of CA-1P may not be due entirely to the substitution pattern in the B-ring of 2,3-diphosphate salt, but rather may be due to a change in pharmacokinetics associated with a Z-stilbenoid compound which incorporates a 3,4,5-trimethoxyphenyl motif in the A-ring, and a 4'-methoxy, 3'-O-Phosphate, along with the incorporation of an additional group (with either an electronic or steric bias) at C-2', C-5', or C-6'. Compounds of this basic structural pattern may demonstrate good bioavailability and favorable pharmacokinetics which result in an improved interaction with tubulin and enhanced efficacy as VTAs. It should be readily apparent to anyone skilled in the art that although the new compounds described herein have a trimethoxyaryl substitution pattern in the A-ring, it is a logical extension to vary the positions of these methoxy groups in the C-2, C-3, C-4, C-5, and C-6 positions. Substitution patterns of this type may also result in compounds active as VTAs.

A variety of studies have suggested that the 3,4,5-trimethoxy substitution pattern on the A-ring and the 4-methoxy moiety on the B-ring are important structural features of the pharmacophore for these stilbenoid analogs (FIG. 3). Accordingly, the inventors have maintained these functionalities in most of the new molecules and have included further substitution patterns around the B-ring. The present invention and the compounds which are a part thereof is not limited in this respect, however, and substitution by other than a 4-methoxy moiety on the B-ring is contemplated. It is the contention of the present inventors that the improved in vivo activity of CA-1P (as related to CA-4P) is not due solely to the presence of a diphosphate moiety, but rather may have a strong tie to the pharmacokinetics of this compound including the enzymatic cleavage of the phosphate group (presumably by nonspecific alkaline phosphatase), subsequent inhibition of tubulin assembly resulting in morphological changes (rounding-up) of the immature endothelial cells lining the microvessels of tumors, and the resulting inability of these microvessels to sustain blood flow. Additional pharmacokinetic parameters such as reversibility of tubulin binding and perhaps incorporation of the parent CA-1 in the cytosolic fluid around the tumor cell itself may also play key biological roles.

SUMMARY OF THE INVENTION

The present invention relates to novel stilbene compounds and more particularly to tubulin-binding stilbenoid analogs structurally related to combretastatin A-1 and A-4. The synthesis of these new compounds is disclosed herein, together with experiments that demonstrate their activity in vitro and in vivo.

In a first aspect the present invention provides a novel stilbene compound represented by the structure:

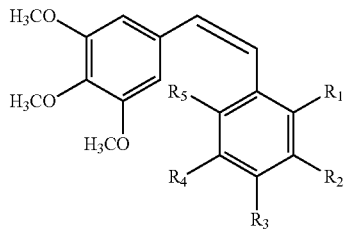

(I)

wherein:

$R_1$, $R_4$ and $R_5$ is independently H, OH, lower alkoxy, $NH_2$, $NO_2$, $N_3$, NH—$R_6$, halogen, a phosphate ester salt moiety of the general formula (—O—(P(O)($O^-M^-$)$_2$, wherein M is a metal cation or salt such as Na, K and Li, or —$OPO_3R_7R_8$;

$R_2$ is H, OH, lower alkoxy, $NH_2$, $NO_2$, NH—$R_6$, or phosphate ester salt moiety of the general formula (O—P(O)($O^-M^+$)$_2$), wherein M is a metal cation or salt such as Na, K and Li; or —$OPO_3R_7R_8$, wherein $NH_2$ or OH may cyclize with $R_1$;

$R_3$ is H, lower alkoxy, or phosphate ester salt moiety of the general formula (—O—P(O)($O^-M^+$)$_2$), wherein M is a metal cation or salt such as Na, K and Li or –$OPO_3R_7R_8$;

$R_6$ is an amino acid acylamino group; and $R_7$ and $R_8$ is independently lower alkyl, cycloalkyl or an ammonium salt ($NH_4^+$).

In a second aspect the present invention provides a novel stilbene compound represented by the structure:

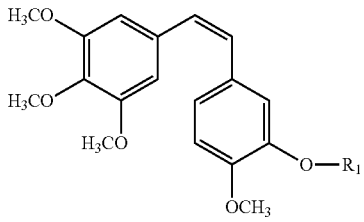

(II)

wherein:

$R_1$ is a phosphate ester salt moiety of the general formula (—P(O)($O^-M^+$)$_2$), wherein M is a metal cation or salt such as Na, K and Li, —$PO_3R_2R_3$—, or an alkyl sulfonate;

$R_2$ is an alkyl group or an ammonium salt ($NH_4^+$); and $R_3$ is an alkyl group or a cycloalkyl.

The compounds of formulas I and II as well as analogs thereof, are vascular targeting agents (VTAs) useful for the treatment of solid tumor cancers and diseases associated with unwanted neovascularization such as retinal neovascularization and restenosis, as well as other conditions of nonmalignant neovascularization. More specifically, the compounds of formula I and II are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer, anaplastic thyroid cancer and Kaposi's sarcoma.

It is thus an object of the present invention to provide a method to reduce or prevent retinal and corneal neovascularization via treatment with a drug that inhibits the assembly of tubulin into microtubules and which are potent vascular targeting agents.

It is also a further object of this invention is to provide a method to reduce or prevent the development of atherosclerosis or restenosis by treatment with a drug which inhibits the assembly of tubulin into microtubules and which are potent vascular targeting agents.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference.

DETAILED DESCRIPTION OF THE FIGURES

Figure 2:
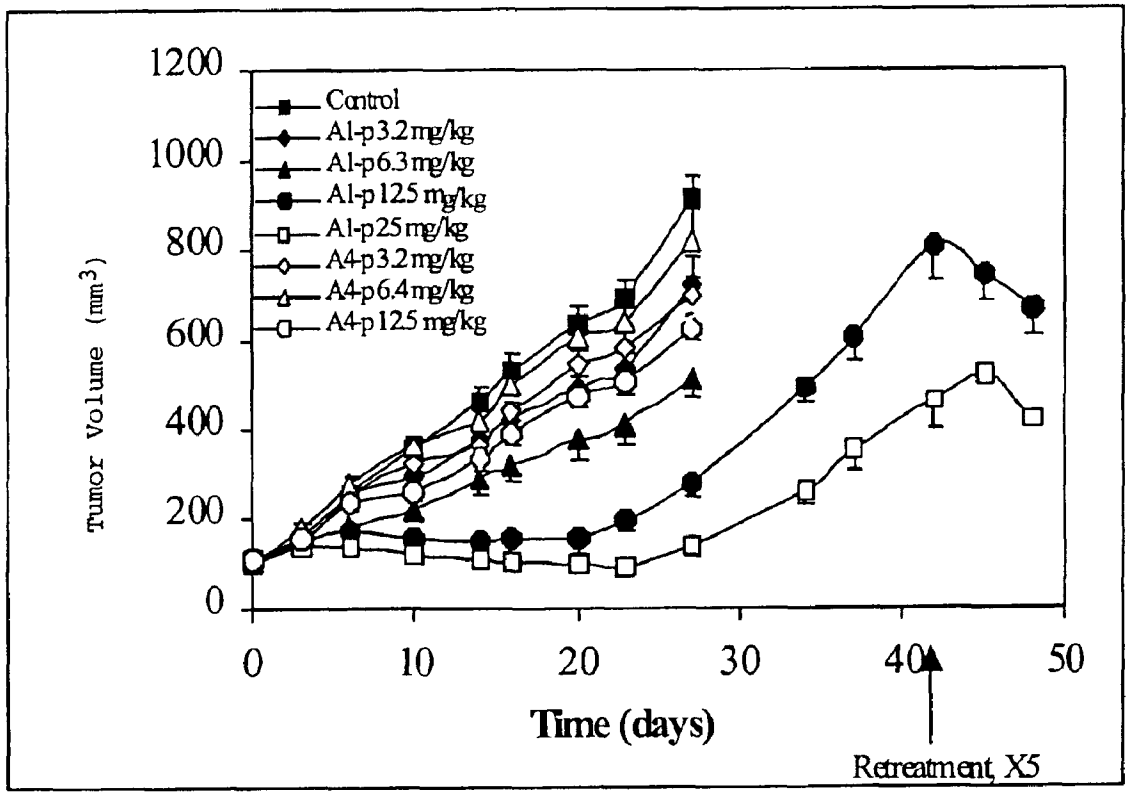

FIG. 1 is a comparison of the effects of CA-4P and CA-1P on tumor blood flow over time. The vascular shutdown capacity of each compound was measured in SCID mice implanted subcutaneously with a murine hemangioendothelioma (MHEC5-T) tumor (n=3). In each case, 100 mg/kg of drug was injected as a single dose, and fluorescent beads were added through a tail vein 3 minutes prior to sacrifice. Blood flow reduction was quantified by fluorescence microscopy and expressed as a percentage of blood flow observed in those animals treated with a saline control;

FIG. 2 is a comparison of the anti tumor growth activity of CA1-P and CA-4P versus control in a nude mouse model of human breast carcinoma. Mice (n=3) were treated once daily (3.2, 6.3, 12.5, or 25 mg/kg) in the first five days of the experiment. Some of the tumors were retreated for another 5 days beginning on day 42 of the experiment; and FIG. 3 is depiction of the salient structural-activity relationship (SAR) features of the stilbenoid VTA pharmacophore. These features are retained in the molecular structure of CA-4 and are important for optimal tubulin-binding and vascular shutdown activity.

DETAILED DESCRIPTION OF THE INVENTION

As defined herein, the present invention provides compounds of formula I and II and analogs and prodrugs thereof, pharmaceutical compositions employing such compounds and methods of using such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valences is assumed to have the hyrdrogen atom to satisfy the valences.

The term alkyl group when used alone or in combination with other groups, are lower alkyl containing from 1 to 8 carbon atoms and may be straight chained or branched. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NH-COOR— or —OCONHR—), urea (—NHCONHR—) or thiol (—SH). Alkyl groups as defined may also comprise one or more carbon to carbon double bonds or one or more carbon to carbon triple bonds.

The preferred alkyl groups contain 1-8 carbon atoms; more preferred alkyl groups contain 1-6 carbon atoms. Alkylene as used herein refers to a bridging alkyl group of the formula $C_nH_{2n}$. Examples include $CH_2$, —$CH_2CH_2$—, —$CH_2CH_2CH_2$— and the like.

As used herein the term "cycloalkyl" is a species of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

As used herein, the term "lower alkoxy" refers to —O—alkyl groups, wherein alkyl is as defined hereinabove. The alkoxy group is bonded to the main chain, aryl or heteroaryl group through the oxygen bridge. The alkoxy group may be straight chained or branched; although the straight-chain is preferred. Examples include methoxy, ethyloxy, propoxy, butyloxy, t-butyloxy, i-propoxy, and the like. Preferred alkoxy groups contain 1-4 carbon atoms, especially preferred alkoxy groups contain 1-3 carbon atoms. The most preferred alkoxy group is methoxy.

As used herein, the term "halogen" or "halo" refers to chlorine, bromine, fluorine or iodine.

As used herein, the term "lower alkylamino" refers to a group wherein one alkyl group is bonded to an amino nitrogen, i.e., NH(alkyl). The NH is the bridge connecting the alkyl group to the aryl or heteroaryl. Examples include NHMe, NHEt, NHPr, and the like.

The amino acid acyl group in the amino acid acylamino group is an acyl group derived from the amino acid. The amino acids may be enumerated by α-amino acids, β-amino acids and γ-amino acids. Examples of preferred amino acids include glycine, alanine, leucine, serine, lysine, glutamic acid, asparatic acid, threonine, valine, isoleucine, ornithine, glutamine, asparagines, tyrosine, phenylalanine, cysteine, methionine, arginine, β-alanine, tryptophan, proline, histidine, etc. The preferred amino acid is serine.

As used herein, the term "prodrug" refers to a precursor form of the drug which is metabolically converted in vivo to produce the active drug. Thus, for example, combretastatin A-4 phosphate prodrug salts or combretastatin A-1 phosphate prodrug salts administered to an animal in accordance with the present invention undergo metabolic activation and regenerate combretastatin A-4 or combretastatin A-1 in vivo, e.g., following dissociation and exposure to endogenous non-specific phosphatases in the body. A phosphate prodrug salt or phosphate ester salt moiety as used interchangeably herein, include those with a phosphate ester salt moiety ($—OP(O)()^{-0+})_2$) or one phosphate triester moiety ($—OP(O)(OR)_2$) or one phosphate diester moiety ($—OP(O)(OR)(O^-M^+)$ where M is a salt and R is chosen to be any appropriate alkyl or branched alkyl substituent (the two R groups may be the same alkyl group or may be mixed), or benzyl, or aryl groups. The salt M is advantageously Na, K and Li, but the invention is not limited in this respect. The phosphate ester salt moiety may also include ($—OP(O)(O\text{-alkyl})_2$ or $(—OP(O)(O—NH_4^+)_2)$.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca or organic amine salts such as those disclosed in PCT International Application Nos. WO02/22626 or WO00/48606.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

The present invention also relates to the administration of a vascular targeting agent, particularly a tubulin binding agent having the chemical structures disclosed herein, for treating malignant or non-malignant vascular proliferative disorders.

Tubulin binding agents inhibit tubulin assembly by binding to tubulin-binding cofactors or cofactor-tubulin complexes in a cell during mitosis and prevent the division and thus proliferation of the cell. Tubulin binding agents comprise a broad class of compounds which inhibit tubulin polymerization, and which generally function as tumor selective vascular targeting agents useful for cancer chemotherapy, as well as for other non-cancer applications such as ocular disease and restenosis.

Vascular Targeting Agents, also known as Vascular Damaging Agents, are a novel class of antineoplastic drugs which attack solid tumors by selectively occluding, disrupting, or destroying the existing vasculature formed by angiogenesis. The cytotoxic mechanism of VTA action is quite divorced from that of anti-angiogenic agents. A single dose of VTA can cause a rapid and irreversible tumor vascular shutdown of existing tumor vasculature, leading eventually to tumor necrosis by induction of hypoxia and nutrient depletion. Other agents have been known to disrupt tumor vasculature but differ in that they also manifest substantial normal tissue toxicity at their maximum tolerated dose. In contrast, genuine VTAs retain their vascular shutdown activity at a fraction of their maximum tolerated dose.

In one embodiment, the present invention is directed to the administration of a vascular targeting agent ("VTA"), particularly a tubulin binding agent, for the treatment of malignant or non-malignant vascular proliferative disorders in ocular tissue.

Neovascularization of ocular tissue is a pathogenic condition characterized by vascular proliferation and occurs in a variety of ocular diseases with varying degrees of vision failure. The administration of a VTA for the pharmacological control of the neovascularization associated with non-malignant vascular proliferative disorders such as wet macular degeneration, proliferative diabetic retinopathy or retinopathy of prematurity would potentially benefit patients for which few therapeutic options are available. In another embodiment, the invention provides the administration of a VTA for the pharmacological control of neovascularization associated with malignant vascular proliferative disorders such as ocular tumors.

The blood-retinal barrier (BRB) is composed of specialized nonfenestrated tightly-joined endothelial cells that form a transport barrier for certain substances between the retinal capillaries and the retinal tissue. The nascent vessels of the cornea and retina associated with the retinopathies are aberrant, much like the vessels associated with solid tumors. Tubulin binding agents, inhibitors of tubulin polymerization and vascular targeting agents, may be able to attack the aberrant vessels because these vessels do not share architectural similarities with the blood retinal barrier. Tubulin binding agents may halt the progression of the disease much like they do with a tumor-vasculature. Local (non-systemic) delivery of tubulin binding agents to the eye can be achieved using intravitreal injection, sub-Tenon's injection, ophthalmic drops iontophoresis, and implants and/or inserts. Systemic administration may be accomplished by administration of the tubulin binding agents into the bloodstream at a site which is separated by a measurable distance from the diseased or affected organ or tissue, in this case they eye. Preferred modes of systemic administration include parenteral or oral administration.

The compounds of the present invention may are also contemplated for use in the treatment of vascular disease, particularly atheroscleorsis and restenosis. Atherosclerosis is the most common form of vascular disease and leads to insufficient blood supply to critical body organs, resulting in heart attack, stroke, and kidney failure. Additionally, atherosclerosis causes major complications in those suffering from hypertension and diabetes, as well as tobacco smokers. Atherosclerosis is a form of chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting, resulting in the death of the tissue served by that artery.

Restenosis, the recurrence of stenosis or artery stricture after corrective surgery, is an accelerated form of atherosclerosis. Recent evidence has supported a unifying hypothesis of vascular injury in which coronary artery restenosis along with coronary vein graft and cardiac allograft atherosclerosis can be considered to represent a much accelerated form of the same pathogenic process that results in spontaneous atherosclerosis (Ip, J. H., et al., (1990) J Am Coll Cardiol, 15:1667-1687; Muller, D. W. M., et al., (1992) J Am Coll Cardiol, 19:418-432). Restenosis is due to a complex series of fibroproliferative responses to vascular injury involving potent growth-regulatory molecules, including platelet-derived growth factor (PDGF) and basic fibroblast growth factor (bFGF), also common to the later stages in atherosclerotic lesions, resulting in vascular smooth muscle cell proliferation, migration and neointimal accumulation.

Restenosis occurs after coronary artery bypass surgery (CAB), endarterectomy, and heart transplantation, and particularly after heart balloon angioplasty, atherectomy, laser ablation or endovascular stenting (in each of which one-third of patients redevelop artery-blockage (restenosis) by 6 months), and is responsible for recurrence of symptoms (or death), often requiring repeat revascularization surgery. Despite over a decade of research and significant improvements in the primary success rate of the various medical and surgical treatments of atherosclerotic disease, including angioplasty, bypass grafting and endarterectomy, secondary failure due to late restenosis continues to occur in 30-50% of patients (Ross, R. (1993) Nature, 362:801-809).

The most effective way to prevent this disease is at the cellular level, as opposed to repeated revascularization surgery which can carry a significant risk of complications or death, consumes time and money, and is inconvenient to the patient.

Microtubules, cellular organelles present in all eukaryotic cells, are required for healthy, normal cellular activities. They are an essential component of the mitotic spindle needed for cell division, and are required for maintaining cell shape and other cellular activities such as motility, anchorage, transport between cellular organelles, extracellular secretary processes (Dustin, P. (1980) Sci. Am., 243: 66-76), as well as modulating the interactions of growth factors with cell surface receptors, and intracellular signal transduction. Furthermore, microtubules play a critical regulatory role in cell replication as both the c-mos oncogene and CDC-2-kinase, which regulate entry into mitosis, bind to and phosphorylate tubulin (Verde, F. et al. (1990) Nature, 343:233-238), and both the product of the tumor suppressor gene, p53, and the T-antigen of SV-40 bind tubulin in a ternary complex (Maxwell, S. A. et al. (1991) Cell Growth Differen., 2:115-127). Microtubules are not static, but are in dynamic equilibrium with their soluble protein subunits, the$\alpha$- and $\beta$-tubulin heterodimers. Assembly under physiologic conditions requires guanosine triphosphate (GTP) and certain microtubule associated and organizing proteins as cofactors; on the other hand, high calcium and cold temperature cause depolymerization.

Interference with this normal equilibrium between the microtubule and its subunits would therefore be expected to disrupt cell division and motility, as well as other activities dependent on microtubules. This strategy has been used with significant success in the treatment of certain malignancies. Indeed, antimicrotubule agents such as colchicine and the vinca alkaloids are among the most important anticancer drugs. These antimicrotubule agents, which promote microtubule disassembly, play principal roles in the chemotherapy of most curable neoplasms, including acute lymphocytic leukemia, Hodgkin's and non-Hodgkin's Lymphomas, and germ cell tumors, as well as in the palliative treatment of many other cancers.

Taxol® (paclitaxel) has been shown to be an effective antimicrotubule agent. Unlike other antimicrotubules such as colchicine and the vinca alkaloids which promote microtubule disassembly, taxol acts by promoting the formation of unusually stable microtubules, inhibiting the normal dynamic reorganization of the microtubule network required for mitosis and cell proliferation (Schiff, P. B., et al. (1979) Nature 277: 665; Schiff, P. B., et al. (1981) Biochemistry 20: 3247). In the presence of taxol, the concentration of tubulin required for polymerization is significantly lowered; microtubule assembly occurs without GTP and at low temperatures, and the microtubules formed are more stable to depolymerization by dilution, calcium, cold, and inhibitory drugs. Taxol will reversibly bind to polymerized tubulin, and other tubulin-binding drugs will still bind to tubulin even in the presence of taxol.

Taxol is, however, highly insoluble and severe allergic reactions have been observed following administration of taxol. Furthermore, cardiac arrhythmias are associated with taxol administration, and like allergic reactions, their incidence is affected by the dosage and rate of taxol administration.

Although others have investigated the use of the antimicrotubule agent colchicine in preventing restenosis, opposite conclusions have been reported (See Currier, et al., "Colchicine Inhibits Restenosis After Iliac Angioplasty In The Atherosclerotic Rabbit" (1989) Circ., 80:II-66; O'Keefe, et al., "Ineffectiveness Of Colchicine For The Prevention Of Restenosis After Coronary Angioplasty" (1992) J. Am. Coll. Cardiol., 19:1597-1600). The art, however, fails to suggest the use of a vascular targeting agent such as CA-1 or CA-4 in preventing or reducing restenosis. Thus, the method of the present invention is to prevent or reduce the development of atherosclerosis or restenosis using a vascular targeting agent such as CA-1 or CA-4 or their analogs, as well as produgs of these compounds. This microtubule stabilizing mechanism of atherosclerosis or restenosis prevention is supported by the analogous results in experiments on cellular proliferation and migration using taxol and $H_2O$ (deuterium oxide), which exert comparable microtubule effects via different underlying mechanisms.

Pharmaceutical compositions of the invention are formulated to be compatible with its intended route of administration. As with the use of other chemotherapeutic drugs, the individual patient will be monitored in a manner deemed appropriate by the treating physician. Dosages can also be reduced if severe neutropenia or severe peripheral neuropathy occurs, or if a grade 2 or higher level of mucositis is observed, using the Common Toxicity Criteria of the National Cancer Institute.

Pharmaceutical compositions for ophthalmic topical administration may include ophthalmic solutions, ophthalmic gels, sprays, ointments, perfusion and inserts. A topically delivered formulation of tubulin binding agent should remain stable for a period of time long enough to attain the desired therapeutic effects. In addition the agent must penetrate the surface structures of the eye and accumulate in significant quantities at the site of the disease. Additionally, a topically delivered agent should not cause an 65 excessive amount of local toxicity.

Ophthalmic solutions in the form of eye drops generally consist of aqueous media. In order to accommodate wide ranges of drugs which have various degrees of polarity, buffers, organic carriers, inorganic carriers, emulsifiers, wetting agents, etc. can be added. Pharmaceutically acceptable buffers for ophthalmic topical formulations include phosphate, borate, acetate and glucoronate buffers, amongst others. Drug carriers may include water, water mixture of lower alkanols, vegetable oils, polyalkylene glycols, petroleum based jelly, ethylcellulose, ethyl oleate, carboxymethylcellulose, polyvinylpyrrolidone, and isoproplyl myristrate. Ophthalmic sprays generally produce the same results as eye drops and can be formulated in a similar manner. Some ophthalmic drugs have poor penetrability across ocular barriers and are not administrable as drops or spray. Ointments may thus be used to prolong contact time and increase the amount of drug absorbed. Continuous and constant perfusion of the eye with drug solutions can be achieved by placing polyethylene tubing in the conjunctival sac. The flow rate of the perfusate is adjustable via a minipump system to produce continuous irrigation of the eye. Inserts are similar to soft contact lens positioned on the cornea, except that inserts are generally placed in the upper cul-de-sac or, less frequently, in the lower conjunctival sac rather than attached to the open cornea. Inserts are generally made of biologically soluble materials which dissolve in lacrimal fluid or disintegrate while releasing the drug.

The compositions of the present invention may also be formulated for systemic administration. Examples of systemic routes of administration include parenteral, e.g., intravenous, intradermal, subcutaneous, oral (e.g., inhalation), transmucosal, and rectal administration. Solutions or suspensions used for parenteral or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a vascular targeting agent) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compound of the present invention may also prove useful in the treatment of coronary artery disease by serving as antimitotic agents coated (or conjugated) onto stents to prevent the recurring problem of restenosis after angioplasty.

In addition to the vascular targeting agents described above, the invention also includes the use of pharmaceutical compositions and formulations comprising a vascular targeting agent in association with a pharmaceutically acceptable carrier, diluent, or excipient, such as for example, but not limited to, water, glucose, lactose, hydroxypropyl methylcellulose, as well as other pharmaceutically acceptable carriers, diluents or excipients generally known in the art.

As used herein, terms "pharmacologically effective amount", "pharmaceutically effective dosage" or "therapeutically effective amount" mean that amount of a drug or pharmaceutical agent that will elicit the biological or medical response of a tissue, system, animal or human that is being sought by a researcher or clinician.

It is intended that the systemic and non-systemic administration of VTAs and tubulin binding agents in accordance with the present invention will be formulated for administration to mammals, particularly humans. However, the invention is not limited in this respect and formulations may be prepared according to veterinary guidelines for administration to animals as well.

The vast majority of the compounds described herein can be prepared synthetically through a Wittig reaction between an appropriately substituted aldehyde and an appropriately substituted phosphorous ylide. The aldehyde portion and ylide portion can be readily switched as well to allow for the judicious incorporation of the requisite functional groups within the target stilbenoids (see Scheme 1 and 2 for general synthetic protocols).

Scheme 1: General Synthetic Route to Stilbenoids -- Part I

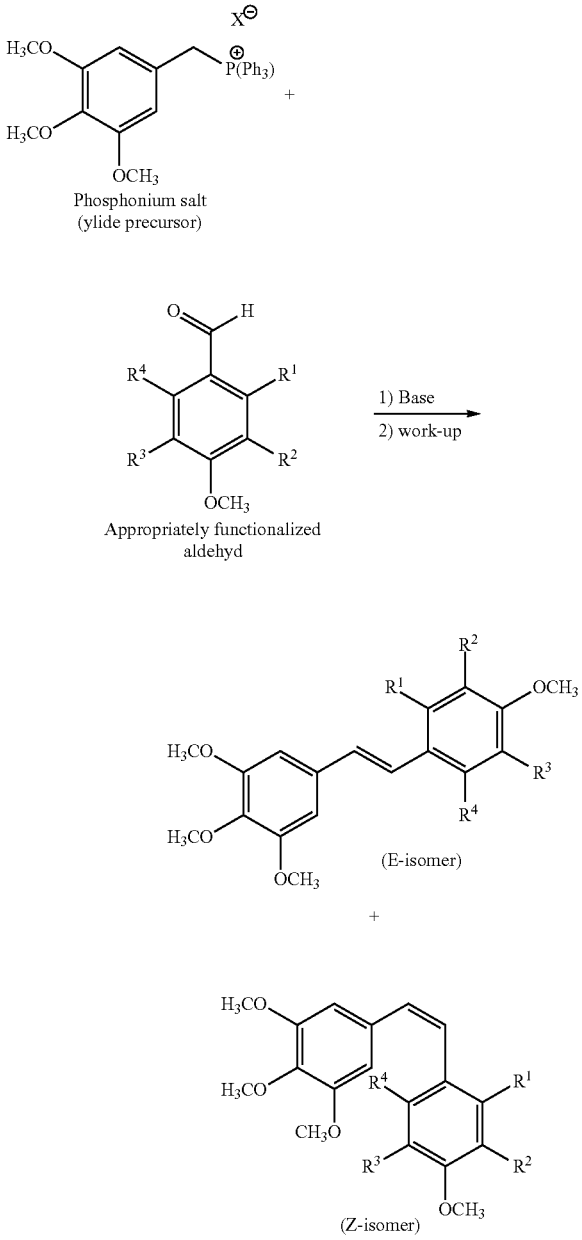

Scheme 2: General Synthetic Route to Stilbenoids -- Part II

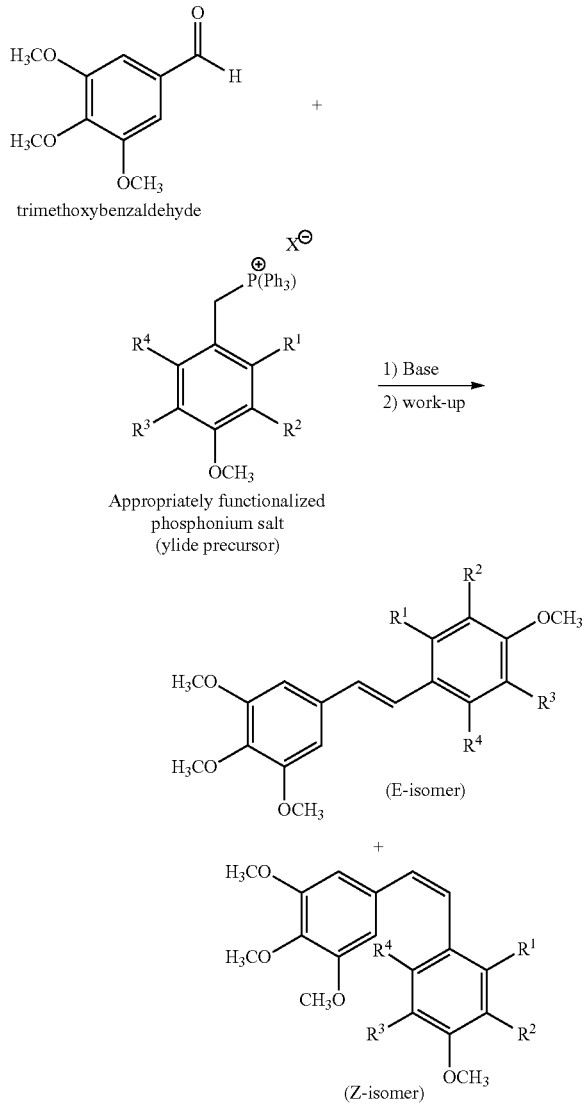

A wide variety of functionalized stilbenoid compounds have been prepared utilizing the general synthetic approach outlined in Schemes 1 and 2. In each case, the starting materials can either be purchased (Aldrich Chemical Co., and/or Acros (Fisher Scientific), etc.) or prepared in one or two steps by routes described in the literature. It is important to note that each of these preferred compounds contains the 3,4,5-trimethoxyphenyl motif in the A-ring of the stilbenoid along with additional functionalization in terms of groups with steric and/or electronic bias at the remaining positions in the B-ring. The preferred stereochemical configuration is Z, however it should be readily apparent to anyone skilled in the art that the corresponding E-isomers will be readily obtained and certain of these E-isomers may have activity as VTAs. In each case, the free phenolic moiety can be readily converted to its corresponding phosphate prodrug entity as exemplified for one of the compounds in Scheme 3. Where more than one free phenolic moiety is present, a mixture of partially phosphorylated compounds can be produced by using limiting amounts of the reagents in Scheme 3

Scheme 3: Representative Synthesis of Stilbenoid Phosphate Prodrug

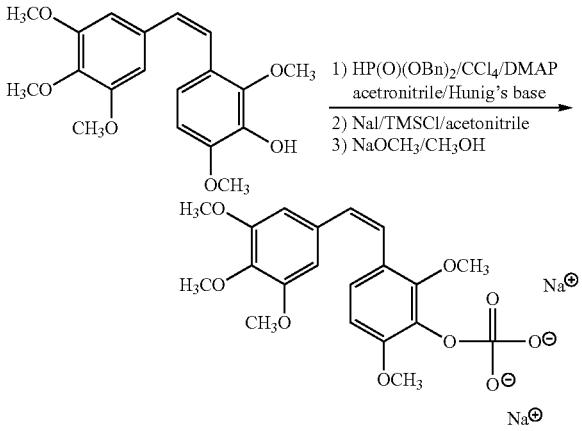

A logical developmental extension of the phenolic stilbenoid analogs is the replacement of the phenol moiety with an amine functionality. This amine can be further modified to form an amide bond to an amino acid residue and function biologically as a prodrug. The parent free amine still functions biologically through a binding interaction with tubulin, while the amide prodrug linkage (serinamide, for example) serves as a prodrug construct. This concept has been successfully developed by Ajinomoto Pharmaceuticals Co., Inc. through the preparation of the 3'-amino analog of CA-4 and its corresponding serinamide. Utilizing similar synthetic methodology as employed by Ajinomoto Inc. (Scheme 4), we have prepared a variety of amine functionalized stilbenoid compounds and their corresponding serinamide congeners.

Scheme 4: Representative preparation of Serinamide Prodrug

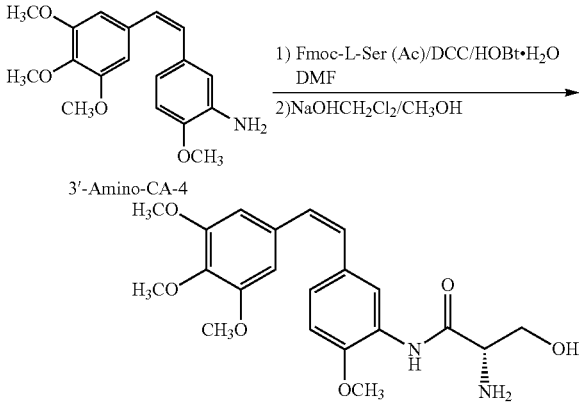

It is important to that certain of these compounds can contain both a serinamide and a phosphate salt or ester. In addition, certain of these compounds can contain a phosphate salt judiciously bridged between a phenol and an amine functionality. It is important to note that although serine may be the preferred amino acid to use in these prodrug formulations, other amino acids may be utilized as well. All of these transformations to prodrugs can be achieved by the methods described herein as well as through the use of other standard synthetic methodologies which should be obvious to anyone skilled in the art.

In an effort to improve the bioavailabilty and pharmacokinetics of stilbenoid derivatives as VTAs, a CA-4P dimer has been prepared (Scheme 5).

Scheme 5: Synthesis of CA-4P Dimer

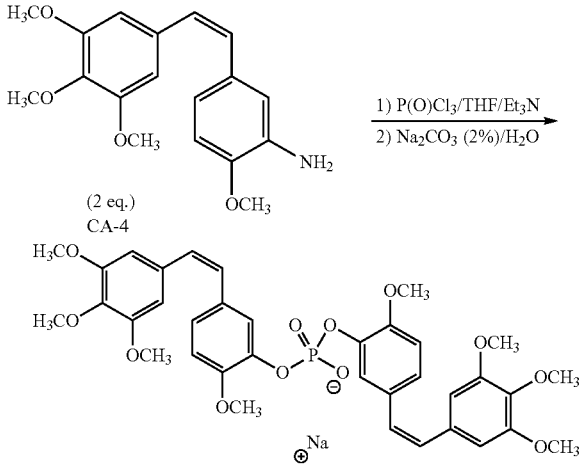

In an analogous manner, a variety of other stilbenoid dimers are anticipated which could be readily prepared by a very similar synthetic strategy to that illustrated in Scheme III. In addition, other salt counter ions such as lithium, potassium, etc. may be employed with presumably equivalent efficacy.

The potential biological advantage of the dimers is based on the following strategy:

A) The dimers may prove to be poorer substrates for enzymatic cleavage by nonspecific alkaline phosphatase or other enzyme B) By slowing down the cleavage of the phosphate (prodrug portion of the molecule), the pharmacokinetics may be altered in a favorable fashion resulting in improved function in terms of vascular targeting C) The dimers are especially attractive due to the fact that enzymatic cleavage delivers two molecules of the biologically potent stilbenoid VTA.

A variety of triester and diester phosphates have been prepared in order to address the issue of improved pharmacokinetics leading to enhanced vascular targeting capability. Several phosphate diester CA4 prodrugs have been prepared based on the promising biological activity displayed by the parent phosphate monoester prodrug, CA4P. A general synthesis for these compounds is detailed in Scheme 6. It should be obvious to anyone skilled in the art that an enormous variety of diesters derived from CA4 (and analogously, derived from other phenolic combretastatins as well as diols such as CA1) can readily be prepared using the methodologies described herein.

Scheme 6: Preparation of Stilbenoid Phosphate Diester Analog

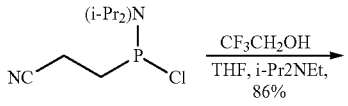

-continued

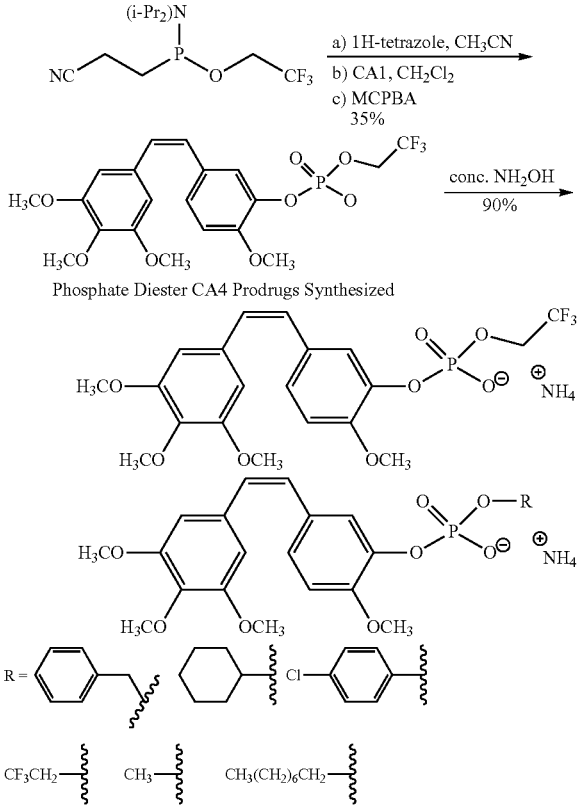

Phosphate Diester CA4 Prodrugs Synthesized

The design premise for these new compounds is similar to that outlined and developed for the stilbenoid dimers (previously described). A similar synthetic strategy was employed for the synthesis of these ligands (see Schemes 6 and 7 for representative examples). The compounds clearly demonstrate reduced cytotoxicity (compared to CA4) which does suggest that they may be poorer substrates for enzymatic cleavage of the phosphate moiety which may prove advantageous for improved VTAs in terms of enhanced in vivo pharmacokinetic profiles.

Scheme 7: Representative Synthesis of Stilbenoid Phosphate Triester

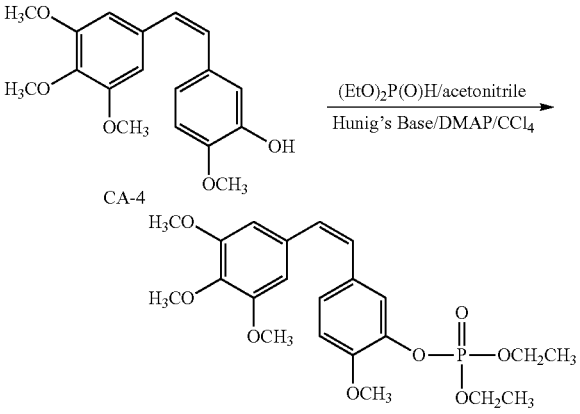

ZSB-11

The invention is further defined by reference to the following examples and preparations which describe the manner and process of making and using the invention and are illustrative rather than limiting. It will be apparent to those skilled in the art that many modifications, both to the materials and methods, may be practiced without departing from the purpose and interest of the invention.

EXAMPLES

Example 1

2'Hydroxy-3'-bromo-3,4,4',5-tetramethoxy-(Z)-stilbene (ZSB-26A)

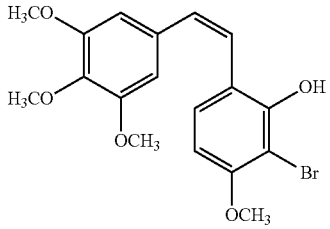

A. Preparation of 3,4,5-trimethoxybenzyltriphenylphosphonium bromide

To a well-stirred solution of $CBr_4$ (5.10 g, 15.4 mmol) in acetone (80 mL) at 0° C. under $N_2$,3,4,5-trimethoxybenzyl alcohol (2.23 g, 11.3 mmol) and triphenylphosphine (4.00 g, 15.3 mmol) were added. After 12 hours, the mixture was filtered through Celite and the solvent removed under reduced pressure to yield benzyl bromide as a brown oil. This oil was then dissolved in $CH_2Cl_2$ (50 mL) and $PPh_3$ (3.25 g, 12.4 mmol) was added. The reaction was heated overnight and then ice-cold water was added and the product isolated by extraction with $CH_2Cl_2$. The organic phase was washed with brine and dried over sodium sulfate. Evaporation of the solvent in vacuo resulted in a crude solid, which was recrystallized from ethyl alcohol/hexane to afford 3,4,5-trimethoxybenzyltriphenyl phosphonium bromide (5.0 g, 85%).

B. Preparation of 2-hydroxy-3-bromo-4-methoxybenzaldehyde

Treatment of 2-hydroxy-4-methoxybenzaldehyde (3.04 g, 20 mmole) with mercuric acetate 1 eq., 20 mmole) in refluxing ethanol(100 ml) containing acetic acid (1% weight percentage) followed by treatment with aq. NaBr gave in 80% yield a mixture of organo-mercusy compounds. The mixture was treated with 1 eq. of Bromine in $CHCl_3$ containing a small amount of acetic acid. Purification over silica gel (elution with 30% EtOAc in hexane, afforded 2-hydroxy-3-bromo-4-methoxybenzaldehyde (2.11 g, 47.2%).

C. Preparation of 2-(t-butyldimethylsilyl)-3-bromo-4-methoxy benzaldehyde

Diiospropylethylamine(3.0 ml ) was added to a stirred solution (under argon) of 2-hydroxy-3-bromo--4-methoxybenzaldehyde(1.96, 8.5 mmole) in DMF (15 ml) followed by t-butyldimethlsilyl chloride(TBSCl, 1.91 g, 12.8 mmole). The reaction mixture was stirred at room temperature for 30 min and Ice (20 g) was added to the mixture. The mixture was then extracted with ether (3×25 ml). The ethereal solution was washed with water (25 ml) and saturated $NaHCO_3$ solution (2×15 ml). The solvent evaporated to yield 2-(t-butyldimethylsilyl)-3-bromo-4-methoxy benzaldehyde as an oil (2.54 g, 7.06 mmole, 83.1%).

D. Preparation of 2'-oxy-(t-butyldimethylsilyl)-3'-bromo-3,4,4',5-tetramethoxy-(Z)-stilbene Butyllithium (1.5 ml, 2M Hexane, 3 mmole) was added (under argon) to a suspension of 3,4,5-trimethoxybenzyltryphenylphosphonium bromide (157 g, 3 mmole) in THF (50 ml) at −15° C. The resulting deep reddish solution was allowed to stir at room temperature for 30 min. 2-hydroxy-3-bromo-4-methoxybenzaldehyde (0.991 g, 2.8 mmole) was added, and the reaction mixture was kept stirring for 3 hours. The reaction mixture was diluted with ice-cold $H_2O$ and extracted with ether (3×25 ml). The etheral solution was washed with water, and solvent was evaporated to yield a Z and E mixture of 2'-oxy -(t-butyldimethylsilyl)-3'-bromo -3,4,4',5-tetramethoxystilbene (1.20 g mixture, 2.36 mmole, 78.7%).

E. Preparation of 2'-hydroxy-3'-bromo-3,4,4',5-tetramethoxy-(Z)-stilbene

To a DMF (7 ml) solution containing Z&E mixture of 2'-oxy -(t-butyldimethylsilyl)-3'-bromo-3,4,4',5-tetramethoxystilbene (743 mg 1.46 mmole), KF (84 mg, 1.46 mmole) and HBr(0.17 ml, 1.46 mmole) was added. The reaction was monitored by TLC. Another 0.17 ml HBr was added in the second day. The reaction was kept stirring for 2 days. Water (15 ml) was added to the solution, and the solution was extracted with ethyl acetate (3×15 ml). The extraction was washed with water, dried with sodium sulfate, and rotavapored. The residue was applied to silica gel column and eluted with hexane:ethyl acetate (7:3) to afford 2'-hydroxy-3'-bromo-3,4,4',5-tetramethoxy-(Z)-stilbene (256 mg 0.64 mmole, 43.8%). H-NMR,(ppm, δ): 6.95,(1H, d, d=11.5 Hz), 6.56(1H, d, J=8.5 Hz), 6.52(1H, d, J=11.5 Hz), 6.44(2H, s), 3.80(3H, s), 3.61(3H, s), 3.54(3H, s) C-NMR,(ppm, δ): 155.00, 153.38, 150.72, 128.40, 126.07, 122.48, 118.59, 133.00, 103.93, 103.49, 60.98, 56.44, 56.15.

Example 2

2'-Disodium Phosphate-3'-bromo-3,4,4',5-tetramethoxy-(Z)-stilbene (ZSB-26B)

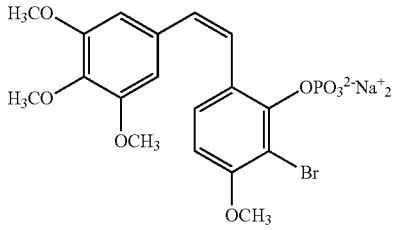

A. Preparation of 2-O-Bis(benzyl)phosphoryl-3-bromo-3,4,4',5-tetramethoxy-(Z)-stilbene 2'-hydroxy-3'-bromo-3,4,4',5-tetramethoxy-(Z)-stilbene (250 mg, 0.63 mmole) was dissolved in acetonitrile(10 ml) in a flask equipped with a septum, thermometer and argon inlet. After cooling to −25° C., carbon tetrachloride(5 eq. 3.15 mmole, 0.6 ml) was added and the solution was stirred for 5 min. With a syringe, diisopropylethylamine (0.65 ml, 2 eq.) was added followed by DMAP(18 mg. 0.3 eq, 0.15 mmole). Slow addition of dibenzyl phosphite(0.25 ml, 1.26 mmole, 2.0 eq.) was begun 1 min later at such a rate the reaction temperature remained below −20° C. After completion of the reaction(in 1 hour by TLC analysis), 0.5M $KH_2PO_4$ was added(5 ml), and the solution was allowed to warm to room temperature and extracted with ethyl acetate (3×20 ml). The combined solvent extract was washed with water (25 ml ) and saturated NaCl (25 ml), then dried. Filtration and removal of solvent gave an oil that was chromatographed on a column of silica gel (hexane:ethyl acetate, 4:1) to give 2-O-Bis(benzyl) phosphoryl-3-bromo-3,4,4',5-tetramethoxy-(Z)-stilbene (390 mg, 94.5%) as a clear gum.

B. Preparation of 2'-Disodium Phosphate-3'-bromo-3,4,4',5-tetramethoxy-(Z)-stilbene Chlorotrimethylsilane (70 mg, 0.648 mmole, 0.082 ml, 2 eq.) was slowly added (with vigorous stirring) to a solution of 2-O-Bis(benzyl)phosphoryl-3-bromo-3,4,4',5-tetramethoxy-(Z)-stilbene (212 mg, 0.324 mmole) and sodium iodide (97.2 mg, 0.648 mmole) in dry acetonitrile (5 ml, in a dry flask under argon). After stirring 20 min, TLC analysis, showed no starting material. Enough water was added to dissolve the salts and a straw color was removed by the addition of 10% aq. sodium thiosulfate (5 drops). The solvent was separated and the aqueous phase extracted with ethyl acetate (4×10 ml). The combined extracted was concentrated in vacuo, and the resulting foam was dissolved in dry methanol(2 ml). Sodium Methoxide(95%, 34 mg, 0.648 mmole) was added in one portion and the solution stirred for 9 hours. The methanol was removed under reduced pressure and the solid recrystallized from water-ethanol to give a white powder (64 mg, 0.12 mmole, 37.0%)

HNMR(ppm, δ): 6.98,(1H, d, d=11.5 Hz), 6.58(1H, d, J=8.5 Hz), 6.50(1H, d, J=11.5 Hz), 6.48(2H, s), 3.83(3H, s), 3.63(3H, s), 3.55(3H, s). PNMR(ppm, δ): −0.36

Example 3

2', 3'-Dinitro-3,4,4',5-tetramethoxy-(Z)-stilbene (ZSB-3B)

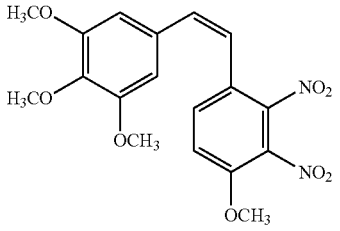

4-methoxy-2,3-dinitrobenzaldehyde (2.94 mmol) and 3,4,5-trimethoxybenzyltriphenyl phosphonium bromide (1.54 g, 2.94 mmol, 1.0 equiv) in anhydrous dichloromethane (25 mL) was added NaH (0.424 g, 17.67 mmol, 6.0 equiv). The reaction mixture was stirred at room temperature for about 7 hours and monitored by TLC. The reaction was quenched by adding water, the organic layer was separated and the aqueous layer was extracted with dichloromethane (3×25 mL). The combined organic layer was washed with brine, dried over $Na_2SO_4$ and concentrated in vacuo to orange colored slush. To this was added about 15 mL of dichloromethane and refrigerated overnight. The crude mixture was subjected to flash chromatography to isolate 2',3'-Dinitro-3,4,4',5-tetramethoxy-(Z)-stilbene (0.581 g, 1.48 mmol, 51%, solid)

$^1$H NMR (300 MHz, $CDCl_3$): δ 3.69 (6H, s), δ 3.82 (3H, s), δ 3.95 (3H, s), δ 6.49 (1H, d, J=11.86), δ 6.77 (1H, d, J=11.84 Hz), δ 7.09 (1H, d, J=8.93 Hz), δ 7.36 (1H, d, J=8.9 Hz).

Example 4

2',3'-Damino-3,4,4',5-tetramethoxy-(Z)-stilbene (ZSB-3B)

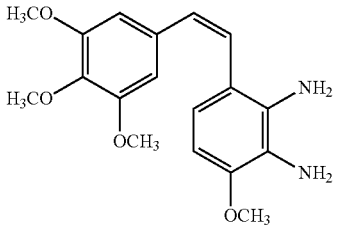

A well-stirred solution of 2',3'-Dinitro-3,4,4',5-tetramethoxy-(Z)-stilbene (0.422 g, 1.08 mmol) in a mixture of acetone-water (2:1) was heated to 50° C. Then sodium thiosulfate (1.88 g, 10.81 mmol, 10.0 equiv) was added and the reaction mixture was heated to reflux for 6 hours. The reaction was cooled to room temperature and water was added. The organic layer was separated and the aqueous layer was extracted with ethyl acetate (4×25 mL). The combined organic layer were washed with brine, dried over $Na_2SO_4$ and concentrated in vacuo. The mixture was then subjected to preparative TLC to give the 2',3'-Diamino-3,4,4',5-tetramethoxy-(Z)-stilbene.

$^1$H NMR (360 MHz, $CDCl_3$): δ 63.61 (6H, s), δ 3.80 (3H, s), δ 3.82 (3H, s), δ 6.38 (1H, d, J=8.44 Hz), δ 6.48 (1H, d, J=12.12 Hz), δ 6.49 (2H, s), δ 6.52 (1H, d, J=12.06 Hz), δ 6.66 Hz (1H, d, J=8.43 Hz).

Example 5

2' serinamide-3,4,4',5-tetramethoxy-(Z)-stilbene (ZSB-45)

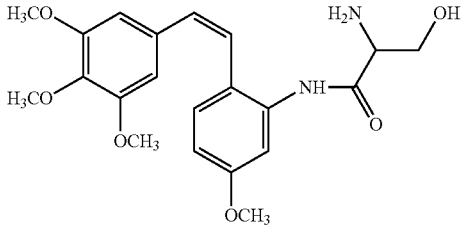

A. Preparation of 2'-FMOC-L-serinamide-3,4,4',5-tetramethoxy-(Z)-stilbene

To a well stirred solution of 2'-amino-3,4,4',5-tetramethoxy-(Z)-stilbene (0.114 g, 0.362 mmol) in anhydrous DMF (2 mL) were added DCC (0.101 g, 0.489 mmol), FMOC (Ac) L-serinamide (0.173 g, 0.467 mmol), and HOBt.$H_2O$ (0.0702 g, 0.520 mmol) at room temperature. After 21.5 h, EtOAc was added and the mixture was filtered. The filtrate was washed 5 times with water and twice with brine and the organic phase was dried over sodium sulfate. After evaporation of the solvent the yellow oil was purified by normal-phase preparative TLC (60% hex-EtOAc) developing twice to afford 2'-FMOC-L-serinamide-3,4,4',5-tetramethoxy-(Z)-stilbene (0.1308 g, 54% yield). $^1$H NMR ($CDCl_3$, 300 MHz) δ 8.13 (br, 1H), 7.91 (s, 1H), 7.77 (d, 2H, J=7 Hz), 7.57 (br, 2H), 7.40 (br, 2H), 7.31 (br, 2H), 7.13 (d, 1H, J=8.5), 6.70 (dd, 1H, J=8.5, 2.4 Hz), 6.32 (br, 2H), 6.22 (s, 2H), 5.27 (m, 1H), 4.54 (m, 2H), 4.40 (m, 1H), 4.19 (m,1H), 3.80 (s, 3H), 3.72 (s, 3H), 3.48 (s, 6H), 1.95 (s, 3H).

B. Prepartion of 2' serinamide-3,4,4',5-tetramethoxy-(Z)-stilbene

2'-FMOC-L-serinamide-3,4,4',5-tetramethoxy-(Z)-stilbene (0.131 g, 0.226 mmol) was dissolved in 1.5 mL of dichloromethane and 1.5 mL of MeOH and 0.22 mL (0.0176 g, 0.44 mmol) of an aqueous solution of 2N- sodium hydroxide were added. After the reaction mixture was stirred at room temperature for 18 h dichloromethane was added and the organic phase was washed once with water and twice with brine, dried under sodium sulfate and the solvent evaporated. The resulting oil was purified by normal-phase preparative TLC (95% $CH_2Cl_2$—MeOH) to afford 2' serinamide-3,4,4',5-tetramethoxy-(Z)-stilbene (52.9 mg, 67%). 1H NMR ($CDCl_3$, 300 MHz) δ 9.65(s, 1H), 8.02 (d, 1H, J=2.6 Hz), 7.15 (d, 1H, J=8.5 Hz), 6.68 (dd, 1H, J=8.5, 2.6 Hz), 6.60(d, 1H, J=12.1 Hz), 6.49 (d, 1H, J=12 Hz), 3.81 (s, 3H), 3.79 (s, 3H), 3.72 (m, 1H), 3.62(m, 1H), 3.60 (s, 6H), 3.36 (t, 1H, J=5.3 Hz), 1.80 (br, 2H). $^{13}$C NMR ($CDCl_3$, 75 MHz) δ 171.8, 159.5, 152.8, 137.7, 135.8, 132.6, 131.8, 130.1, 124.3, 119.9, 110.9, 105.8, 105.2, 65.1, 60.9, 56.5, 55.9, 55.5.

Example 6

CA-4P Methyl Ester, Ammonium Salt (Oxi-com-209)

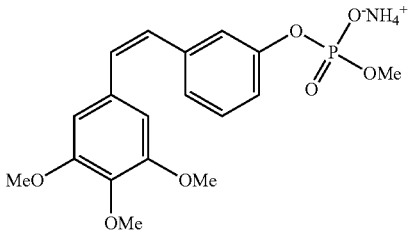

Step A 0.60 ml (2.69 mmol) of 2-cyanoethyl diisopropylchlorophosphoramidite, 0.90 ml (5.2 mmol) dry Hunig's base and 0.14 ml (3.46 mmol) anhydrous methanol (Aldrich) were reacted in 15 ml dry THF under argon with stirring. The reaction was allowed to proceed for over 20 hours and monitored by TLC (a white-orange spot on staining with ninhydrin that follows the solvent front for a 50:50 mix of ethyl acetate-hexanes, or has an Rf=0.12 in 5% ethyl acetate in hexanes). After this about 2.5 g of silica gel that had previously been neutralized with triethylamine was then added to the reaction mixture and the solid products were adsorbed onto the silica gel by removing the solvents by rotovaporization. The dried down silica gel was collected into a Biotage FLASH sample injection (SIM) cartridge and eluted through a silica gel packed FLASH 20S column with 7% ethyl acetate in hexanes on a Biotage FLASH 40 chromatography system, pressure=15 psi. (Note: Before sample elution the column was prepared by neutralizing the silica gel in it with approximately 250 ml of a 15% triethylamine-methanol solution after which it was rinsed with about 100 ml of the 7% ethyl acetate in hexanes solution). Fractions 6 to 10 were pooled and rotovaporized to give 0.372 g (1.60 mmol) of product in 60% yield (to the initial chlorophosphoramidite).

Step B 0.3551 g (1.529 mmoles) of product from Step 1 was added to 4.0 ml (1.8 mmol) of a 0.45 M 1H-tetrazole solution in acetonitrile (Fluka) in a stoppered round-bottom flask under argon. Next, 3.7 ml (0.1515 g/ml=0.56 g, 1.70 mmol) of a Combretastatin A4 (CA4) solution in dry methylene chloride was added slowly from a syringe dropwise to this solution under argon with stirring. The reaction was monitored by TLC using a 50:50 ethyl acetate-hexanes mixture, Rf of product=0.70 (visible by uv, turns brown by air oxidation of CA4 group and also develops orange with ninhydrin) and allowed to react for about 33 hours.

Step C

After this 0.449 g of (~2 mmol) m-choroperoxybenzoic acid (70-75%, Acros) was added to the reaction mixture and product formation was monitored by TLC as before. Almost complete conversion to the oxidized diester was evident in 10 minutes, but the reaction was run for 2 hours. TLC monitoring of the product showed a broad spot with an Rf of about 0.30 in 50:50 ethyl acetate-hexanes. The product was purified by flash column chromatography to give 0.250 g (0.540 mmol, 35% yield) of product shown pure by 1-H and 31-P NMR.

Step D 0.2122 g (0.4598 mmol) of pure product from Step 3 was dissolved in 10 ml of an 80:20 methanol-methylene chloride solution to which was added 0.15 ml (1.14 mmol, ~2.5 equivalents) concentrated ammonia solution (28-30% ammonia, Acros) which was allowed to react for over 24 hours. The 3-aminopropionitrile by-product, ammonia and solvents were removed by rotovaporation and then vacuum pump. This gave the correct product in about 90% yield verified by 1-H and 31-P NMR and greater than 90% in purity by HPLC and capillary gel electrophoresis.

Using the procedures described herein or by modification of the procedures described herein as known to one of ordinary skill in the art, the following additional compounds have been prepared:

2'-Disodium Phosphate-3'-Hydroxy-3,4,4',5-tetramethyl-(Z)-stilbene (ZSB-1A)

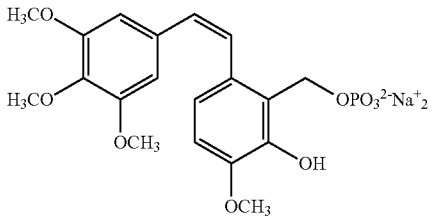

2'-Hydroxy-3'-Disodium Phosphate-3,4,4',5-tetramethoxy-(Z)-stilbene (ZSB-2A)

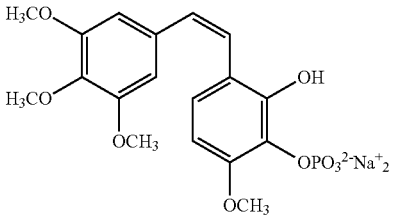

3',5'-Dihydroxy-3,4,4',5-tetramethoxy-(Z)-stilbene (ZSB-1B)

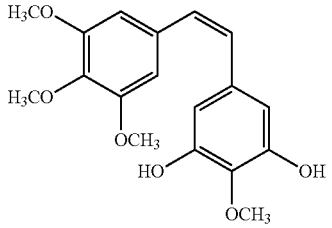

(0.27 g, 80%). $^{1}$H NMR (300 MHz): 3.67(6H, s), 3.79(3H, s), 3.86(3H, s), 4.96(2H, bs), 6.23(1H, d, J=12.28 Hz), 6.36(1H, d, J=12.2 Hz), 6.43(2H, s), 6.56(2H, s). $^{13}$C NMR (75.47 MHz): 55.92, 60.94, 61.14, 106.2, 108.68, 129.19, 130.07, 132.29, 133.69, 134.02, 137.27, 148.62, 152.83.

3',5'-Tetrasodium Phosphate-3,4,4',5-tetramethoxy-(Z)-stilbene (ZSB-2B)

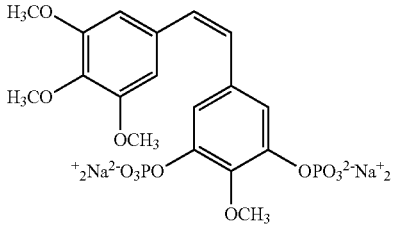

2'-Bromo-3'-Hydroxy-3,4,4',5-tetramethoxy-(Z)-stilbene (ZSB-16)

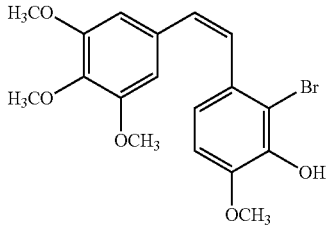

(530 mg, 51.5%, solid). HNMR (ppm, δ): 6.83(1H, d, J=8.5), 6.70(1H, d, J=8.5 Hz), 6.56(2H, s), 6.42(2H, s), 3.94(3H, s), 3.88(3H, s), 3.65(6H, s) CNMR(ppm, δ): 153.13, 146.36, 143.54, 137.54, 132.43, 131.52, 131.10, 129.14, 121.97, 110.61, 109.87106.44, 61.30, 56.83, 56.22

2'-Bromo-3'-Disodium Phosphate-3,4,4',5-tetramethoxy-(Z)-stilbene (ZSB-17)

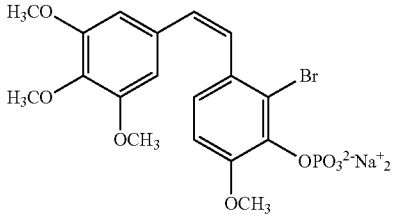

(120.2 mg, 0.2.3 mmol, 71.4%) $^{1}$H-NMR(ppm, δ): 6.67(1H, q), 6.52(1H, d, J=11.9 Hz), 6.43(1H, d, J=12.4 Hz), 6.36(2H, s), 3.63(3 H,s), 3.55(6H, s), 3.47(3H, s) $^{13}$-CNMR(ppm, δ, CDCl3): 152.32, 133.50, 130.96, 130.74, 129.96, 125.06, 111.69, 106.71, 61.17, 56.11. P-NMR (ppm, δ): 1.06.

2'-hydroxy-3,3',4,4',5-pentamethoxy-(Z)stilbene (ZSB-18)

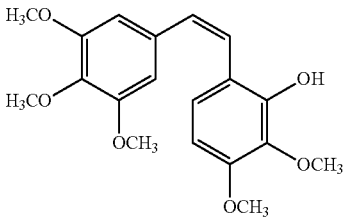

(1.49 g 4.3 mmol, 82.7%) HNMR(ppm, δ, CDCl3): 7.27 (1H, d, J=12.3 Hz), 7.08(1H, d, J=8.3 Hz), 7.03(1H, d, J=13.5 Hz), 6.75(2H, s), 6.53(1H, d, J=8.6 Hz), 3.92(6H, s), 3.90 (6H, s), 3.88(3H, s). CNMR(ppm, δ, CDCl3): 153.70, 152.05, 147.73, 137.83, 135.86, 134.36, 128.09, 123.12, 122.15, 118.11, 104.43, 103.66, 61.39, 56.50, 56.27.

2'-Disodium Phosphate-3,3',4,4',5-pentamethoxy-(Z) stilbene (ZSB-19)

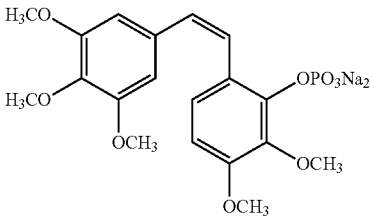

(97 mg, 0.21 mmol, 42%, solid) $^{1}$H-NMR(ppm, δ, D2O): 7.25(1H, d, J=12.3 Hz), 7.08(1H, d, J=8.3 Hz), 6.93(1H, d, J=13.6 Hz), 6.83 (1H, d, J=8.6 Hz), 6.71(2H, s). PNMR (ppm, δ, D2O): 2.97

3'-hydroxy-3,4,4',5,5'-pentamethoxy-(Z)stilbene (ZSB-20)

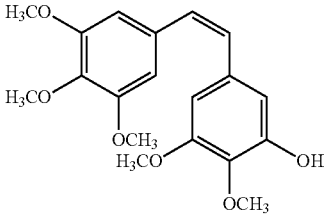

(560 mg 1.62 mmole, 62.3%). $^{1}$H-NMR (ppm,δ,CDCl3): 6.88(2H, s), 6.80(1H, s), 6.72(2H, s), 6.63(1H, s), 3.92(12H, s), 3.86(3H,s) C-NMR(ppm, δ, CDCl3): 153.79, 152.84, 149.83, 135.70, 133.83, 133.37, 128.70, 128.30, 106.47, 103.84, 102.86, 61.40, 60.83. 56.52, 56.27.

3'-Hydroxy-2',3,4,4',5-pentamethoxy-(Z)-stilbene (ZSB-27A)

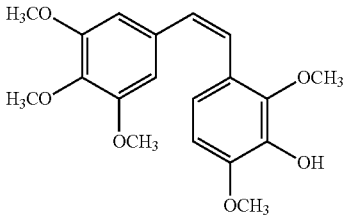

(251.5 mg, 0.726 mmol, 72.6%) $^{1}$H-NMR (300 MHz, $CDCl_3$): δ 6.73 (d, J=8.7 Hz, 1H), 6.58 (d. J=12.3 Hz, 1H), 6.52-6.44 (m, 4H), 5.80 (s, 1H), 3.85, 3.79 (s,s, 9H), 3.63(s, 6H).$CDCl_3$): δ 153.1, 147.5, 145.8, 138.9, 137.4, 133.0, 130.4, 125.4, 124.2, 120.9, 120.6, 106.8, 106.4, 61.3, 61.2, 56.7, 56.6, 56.2.

3'-Disodium Phosphate-3,3',4,4',5-pentamethoxy-(Z)-stilbene (ZSB 27B)

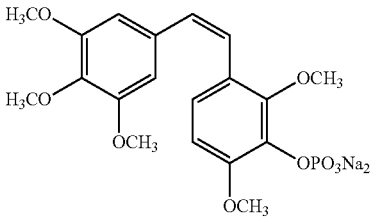

(117.8 mg, 0.25 mmol, 73.7%, solid). $^{1}$H-NMR (300 MHz, D2O): δ 6.70 (d, J=8.4 Hz, 1H), 6.55 (d,d J=12.1 Hz, 5.5 Hz, 1H), 3.70, 3.56, 3.48, (s,s,s, 15H). $^{13}$C-NMR (300 MHz, D2O): δ 153.2, 152.3, 150.9, 137.1, 136.9, 136.0, 134.0, 126.5, 124.2, 124.1, 108.3, 106.7, 61.2, 61.1, 56.2, 56.1. $^{31}$P-NMR (300 MHz, $D_2O$): δ 1.43

4'-hydroxy-2'-Iodo-3,4,5,5'-tetramethoxy-(Z)-stilbene (ZSB-29A)

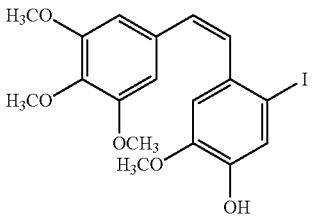

(0.72 g, 1.5 mmol, 88%, oil). $^{1}$H-NMR ($CDCl_3$, 300 MHz): δ 3.67 (s, 3H); 3.73 (s, 6H); 3.84 (s, 3H); 6.09 (s, 1H); 6.39 (d, J=12.1, 1H); 6.47 (d, J=12.1, 1H); 6.53 (s, 2H); 6.74 (d, J=1.6, 1H); 7.30 (d, J=1.6, 1H).

4'-Disodium Phosphate-2'-Iodo-3,4,5,5'-tetramethoxy-(Z)-stilbene (ZSB-29B)

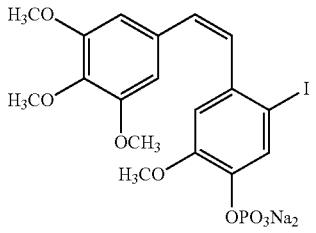

2',5'-Dihydroxy-3,4,4',5-tetramethoxy-(Z)-stilbene (ZSB-33A)

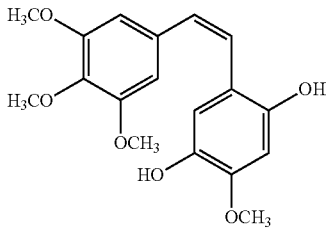

2',5'-Tetrasodium Diphosphate-3,4,4',5-tetramethoxy-(Z)-stilbene (ZSB-33B)

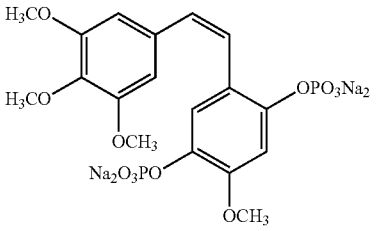

2',3'-Dihydroxy-3,4,5-trimethoxy-(Z)-stilbene (ZSB-36A)

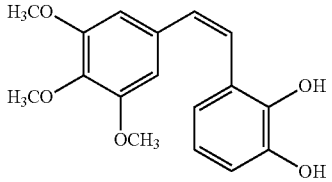

(0.5 g, 1.65 mmol, 43.3%) $^1$H-NMR ($CDCl_3$, 300 MHz): δ 3.63 (6H,s,2*$OCH_3$); 3.83(3H, s, $OCH_3$), 5.10 (1H,s, OH), 5.50 (1H,s,OH), 6.47 (2H,s,H-2,H-6), 6.53 (1H,d,J=12.04 Hz, —CH═CH—), 6.60 (1H,d,J=12.06 Hz, —CH═CH—), 6.92 (3H,m,H-4',H-5',H-6').

2',3'-Diphosphate-3,4,5-trimethoxy-M-stilbene (ZSB-36B)

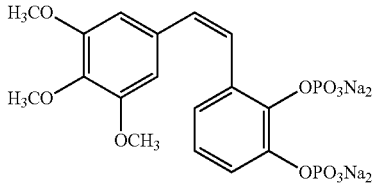

(0.036 g, 0.071 mmol, 59.1%, solid) $^1$H-NMR (300 MHz, D2O): δ 3.69 (6H,s,2*$OCH_3$); 3.77 (3H, s, $OCH_3$), 6.66 (2H, s, H-2,H-6), 6.73 (1H,d,J=12.02 Hz, —CH═CH—), 6.86 (1H,d,J=12.21 Hz, —CH═CH—), 6.98 (2H,m,H-5', H-6'), 7.24 (20H, m, 4*C6H6), 7.36 (1H,d,J=7.14 Hz, H-4') PNMR (300 Mhz, D2O) δ −3.27, −3.88.

3',4'Dihydroxy-3,4,5-trimethoxy-(Z)-stilbene (ZSB-37A)

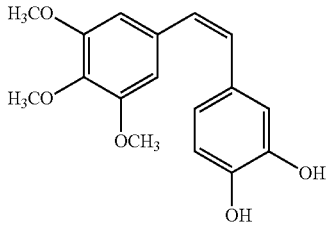

3',4'Diphosphate-3,4,5-trimethoxy-(Z)-stilbene (ZSB-37B)

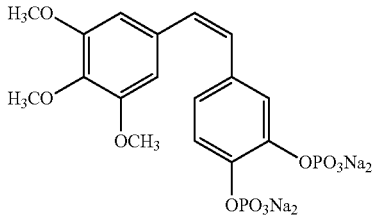

$^1$H-NMR (ppm, δ, D2O): 6.77 (1H,s); 6.73 (2H, q); 6.52 (2H, s); 6.46 (1H,d,J=12.1 Hz), 6.41 (1H,d, J=12.1, 1H), 3.88 (3 H,s), 3.72 (6H,s). PNMR (ppm, δ, D2O): −3.69.

4'-hydroxy-3,4,5-trimethoxy-(Z)-stilbene (ZSB-40A)

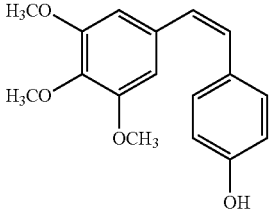

(ZSB-40B) 4'-phosphate-3,4,5-trimethoxy-(Z)-stilbene

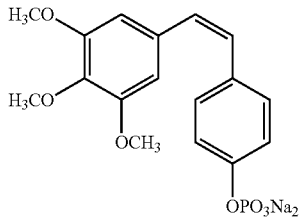

(85 mg, 0.20 mmol, 30.0%). $^{1}$H-NMR (ppm, δ): 7.13 (1H,d, J=8.3 Hz), 7.00(1H,d, J=8.3 Hz), 6.59 (2H,s), 6.56 (1H,d, J=13.00), 6.45(1H,d,J=12.1 Hz), 3.67(3H,s). $^{13}$C-NMR (ppm, δ): 153.00, 133.50, 130.00, 129.80, 129.76, 125.00, 120.05, 119.50, 108.00, 106.44, 61.00, 56.01. PNMR (ppm, δ): 0.10.

2'-Fluoro-3'-Hydroxy-3,4,4',5-tetramethoxy-(Z)-stilbene (ZSB-41A)

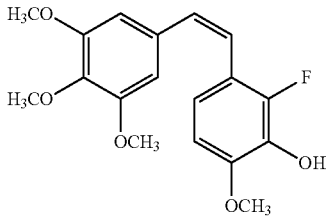

(126 mg, 0.37 mmol, 74.8%). $^{1}$H-NMR (300 MHz, $CDCl_3$): δ 6.79 (t, J=8.4 Hz, 1H), 6.57-6.50 (m, 5H), 3.86(s, 3H), 3.85 (s, 3H), 3.80,(s, 6H). $^{13}$C-NMR (300 MHz, $CDCl_3$): δ 153.2, 150.6, 147.9, 147.4, 137.6, 134.4, 134.2, 132.8, 131.6, 122.33, 122.29, 120.27, 1 119.25, 119.08, 106.3, 61.29, 56.78, 56.25

(ZSB-41B) 2'-Fluoro-3'-Disodium Phosphate-3,4,4',5-tetramethoxy-(Z)-stilbene

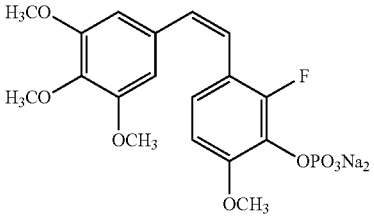

2'-Hydroxy-3,4,4',5-tetramethoxy-(Z)-stilbene (ZSB-46A)

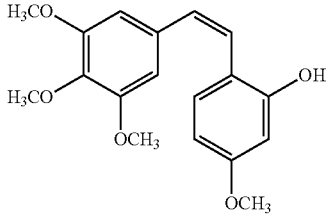

(620 mg, 55%, solid). HNMR(ppm, δ, CDCl3): 7.43(1H, J=8.6 Hz), 7.20(1H, d, J=16.3 Hz), 6.94(1H, d, J=16.3 Hz), 6.74(2H, s), 6.55(1H, d, J=8.3 Hz), 3.92(6H, s), 3.88(3H, s), 3.81(3H, s).

2'-Disodium Phosphate-3,4,4',5-tetramethoxy-(Z)-stilbene (ZSB-46B)

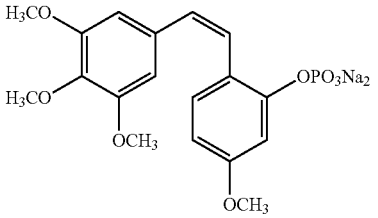

HNMR(ppm, δ, D2O): 7.49(1H,d0, 7.36 (1H,d), 6.94 (4H, m), 6.57 (4H,d), 3.77(6H,s), 3.71(3H,s), 3.65 (3H,s). PNMR (ppm, δ, D2O): 1.26.

3,5-Dinitro-3,4,4',5'-tetramethoxy-(Z)-stilbene (ZSB-13)

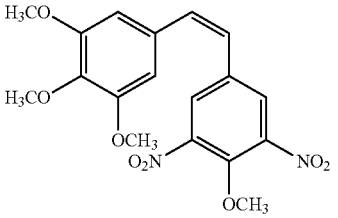

3',5'-Diamine-3,4,4',5-tetramethoxy-(Z)-stilbene (ZSB-14)

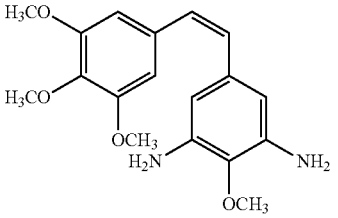

$^{1}$H NMR ($CDCl_3$, 360 MHz) δ 6.56 (s, 2H), 6.41 (d, 1H, J=12.2 Hz), 6.34 (d,1H, J=12.2 Hz), 6.14 (s, 2H), 3.82 (s, 3H), 3.72 (s, 3H), 3.70 (s, 6H).

3',5'-Diserinamide-3,4,4',5-tetramethoxy-(Z)-stilbene (ZSB-15)

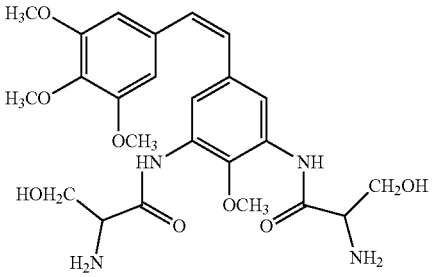

2'-Nitroso-3'hydroxy-3,4,4',5-tetramethoxy-(Z)-stilbene (ZSB-28A)

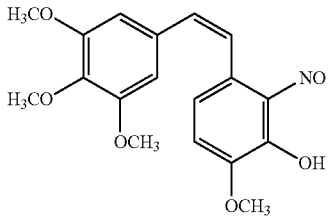

(80 mg, 0.23 mmole, 65%, solid) $^1$H NMR: 3.64 (s, 6H, 2×$OCH_3$); 3.81 (s, 3H, $OCH_3$); 3.92 (s, 3H, $OCH_3$); 6.30 (s, 2H, aryl); 6.59 (d, J=12, 1H); 6.68 (d, J=12, 1H); 6.78(b, J=8.4, 1H); 6.92 (d, J=8.4, 1H).

2'-Nitro-3,4,4',5-tetramethoxy-(Z)-stilbene (ZSB-39A)

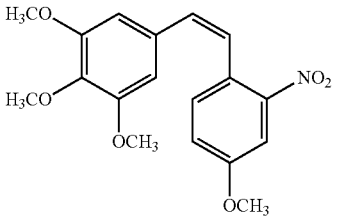

(5.29 g, 81% yield) $^1$H NMR ($CDCl_3$, 300 MHz) δ 7.59 (d, 1H, J=2.7 Hz),7.24 (d, 1H, J=8.8 Hz), 7.01 (dd, 1H, J=8.7, 2.7 Hz), 6.80 (d,1 H, J=11.9 Hz), 6.62 (d, 1H, J=12.0 Hz), 6.28 (s, 2H), 3.93 (s, 3H), 3.86 (s, 3H), 3.62 (s,6H).

2'-Amino-3,4,4',5-tetramethoxy-(Z)-stilbene (ZSB-39B)

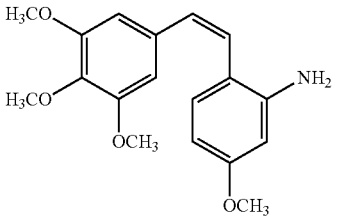

(0.817 g, 38%). $^1$H NMR ($CDCl_3$, 360 MHz) δ 7.03 (d, 1H, J=8.4 Hz), 6.51 (s,2H), 6.49 (d,1H, J=11.6 Hz), 6.42 (d, 1H, J=12 Hz), 6.30 (dd, 1H, J=8.4, 2.5 Hz), 6.25 (d, 1H, J=2.4 Hz), 3.80 (s, 3H), 3.75 (s, 3H), 3.64 (s, 6H), 1.55 (br, 1H).

2'-Serinamide-3,4,4',5-tetramethoxy-(Z)-stilbene (ZSB-45)

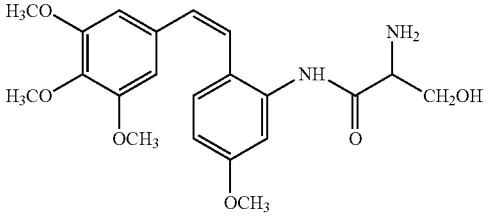

(0.817 g, 38%). $^1$H NMR ($CDCl_3$, 360 MHz) δ 7.03 (d, 1H, J=8.4 Hz), 6.51 (s,2H), (d,1H, J=11.6 Hz), 6.42 (d, 1H, J=12 Hz), 6.30 (dd, 1H, J=8.4,2.5 Hz), 6.25 (d, 1H, J=2.4 Hz), 3.80 (s, 3H), 3.75 (s, 3H), 3.64 (s, 6H), 1.55 (br, 1H).

3'-Hydroxy, 5'-Nitro-3,4,4',5-tetramethoxy-(Z)-stilbene (ZSB-43)

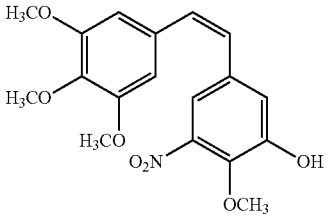

$^1$H NMR ($CDCl_3$, 300 MHz): 3.72 (s, 6H), 3.85 (s, 3H), 3.94 (s, 3H), 6.42 (d, 1H, J=12.1 Hz), 6.47 (s, 2H), 6.61 (d, 1H, J=12.1), 7.16 (d, 1H, J=2.0 Hz), 7.39 (d, 1H, J=2.0 Hz). $^{13}$C NMR ($CDCl_3$, 75 MHz): 56.04, 61.00, 62.54, 106.06, 117.286, 120.73, 126.81, 131.34, 132.38, 133.92, 137.92, 139.80, 142.64, 150.15, 153.18.

3'-Hydroxy, 5'-Amino-3,4,4',5-tetramethoxy-(Z)-stilbene (ZSB-44)

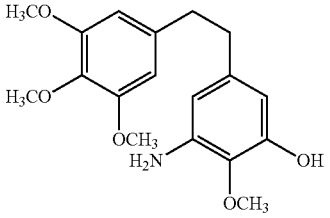

(60 mg, 15%, oil). $^1$H NMR ($CDCl_3$, 300 MHz): 3.71 (s, 6H), 3.78 (s, 3H), 3.84 (s, 3H), 6.27 (d, 1H, J=1.9), 6.35 (d, 1H, J=1.9), 6.41 (d, 2H, J=1.5), 6.54 (s, 2H).

2'-Amino-3'hydroxy-3,4,4',5-tetramethoxy-(Z)-stilbene (ZSB-48)

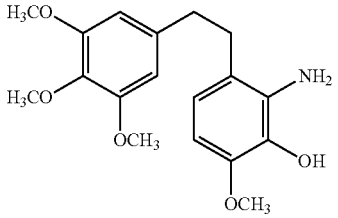

(90.5 mg, 82%, oil) $^1$H NMR ($CDCl_3$, 300 MHz): 3.64 (s, 6H), 3.81 (s, 3H), 3.84 (s, 3H), 6.32 (d, 1H, J=8.4), 6.45 (d, 1H, J=12.1), 6.51 (d, 1H, J=12.0), 6.51 (s, 2H), 6.68(d, 1H, J=8.4). $^{13}$C NMR ($CDCl_3$, 75 MHz): 55.7, 56.1, 60.8, 101.1, 105.9, 117.6, 120.1, 125.7, 130.9, 132.1, 132.2, 132.6, 137.2, 145.7, 152.7.

CA4P Diethyl Ester (Oxi-com 157)

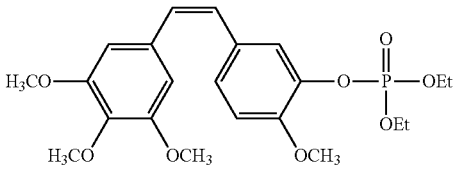

CA4P Dimethyl Ester (Oxi-com 184)

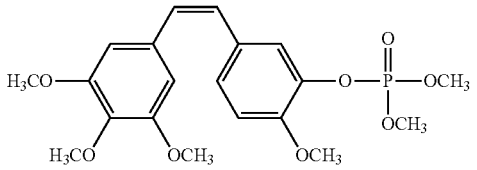

CA4P Cyclohexane Ester, Ammonium Salt (Oxi-com 191)

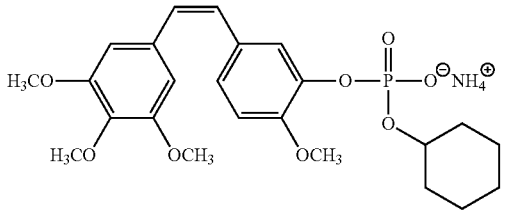

CA4P 4-Chlorobenzyl Ester, Ammonium Salt (Oxi-com-192)

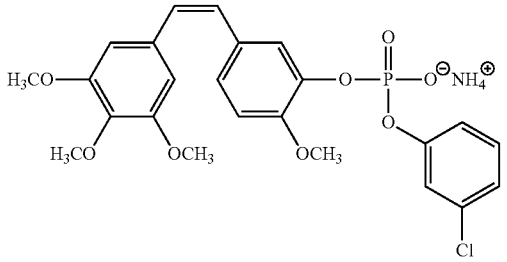

CA4P n-Octyl Ester, Ammonium Salt (Oxi-com 210)

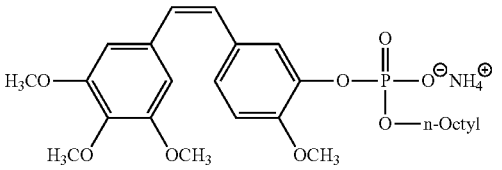

CA4P Trifluoroethane Ester, Ammonium Salt (Oxi-com 211)

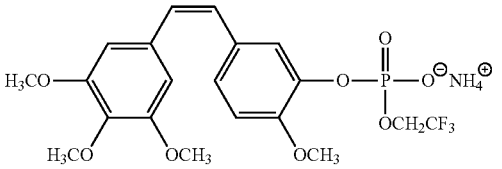

Biological Activity

The pharmacological properties of the compounds of this invention may be confirmed by a number of pharmacological assays. The exemplified pharmacological assays have been carried out with several of the compounds of the present invention.

A. MIT Cytotoxicity Assay

Exponentially growing were treated with the following compounds for 1 hour and 5 days. Insoluble compounds were formulated in a small amount (0.3%) of DMSO for biological evaluation. Cell viability was determined by the calorimetric MTT assay using 3(4,5-dimethylthiazol-2-yl)-2,5-diphenyl-2H-tetrazolium bromide according to well-established procedures (see Berridge, et al. (1996) for a general protocol of this type of assay). The results are shown in Table 2.

TABLE 2

| Compound | IC50 @ 1 h (uM) | IC50 @ 5 days (uM) |
|---|---|---|
| ZSB-213 | 25 | 1 |
| ZSB-3B | 2.4 | 0.0043 |
| ZSB-16 | 2 | 0.0067 |
| ZSB-26A | 3.07 | 0.016 |
| ZSB-27 | 16 | 0.016 |
| ZSB-39 | 2 | 0.008 |
| ZSB-41A | 8 | 0.015 |
| ZSB-43 | 8 | 1.3 |
| ZSB-45 | 10 | 0.05 |
| ZSB-46A | 43 | 0.068 |
| Oxi-com183 | 8 | 0.26 |
| Oxi-com191 | 35 | 0.13 |
| Oxi-com209 | 38 | 0.07 |
| Oxi-com210 | 25 | 0.07 |

B. Vascular Shutdown Assay

The vascular effects of the following compounds were assessed in tumor-bearing mice using a fluorescent-bead assay. A MHEC-5T hemangioendothelioma tumor model was established by subcutaneous injection of $0.5\times10^6$ cultured MHEC5-T cells into the right flank of Fox Chase CB-17 SCID mice and allowed to grow to a size of 300 $mm^3$ before i.p. injection with a single dose of saline control or compound. At 24 hours post-treatment, mice were i.v. injected with 0.25 ml of diluted FluoSphere beads (1:6 in physiological saline) in the tail vein, and sacrificed after 3 minutes. Tumor cryosections at a thickness of 8 um were directly examined using quantitative fluorescent microscopy. For quantification, image analysis of 3 sections from three tumor treated in each group were examined and vascular shutdown was expressed a vessel area per tissue area ($mm^2$) in percentage of the control. The results are shown in Table 3.

TABLE 3

| Compound | % Blood Flow Shutdown (100 mg/kg) |
|---|---|
| ZSB-2B | 65 |
| ZSB-21 | 46 |
| ZSB-27B | 41 |
| ZSB-29B | 43 |
| ZSB-33B | 51 |
| ZSB-39B | 50 |
| ZSB-45 | 43 |
| Oxi-com192 | 90 |
| Oxi-com210 | 89 |

OTHER EMBODIMENTS

It is to be understood that while the invention has been described in conjunction with the detailed description thereof, the foregoing description is intended to illustrate and not limit the scope of the invention, which is defined by the scope of the appended claims.

It is also to be understood that the drawings are not necessarily drawn to scale, but that they are merely conceptual in nature.

The following references are incorporated herein by reference in their entirety:

Aleksandrzak, K., et al., (1998). "Antimitotic Activity of Diaryl Compounds with Structural Features Resembling Combretastatin A-4." Anti-Cancer Drugs 9: 545-550.

Bedford, S. B., et al., (1996). "Synthesis of Water-Soluble Prodrugs of the Cytotoxic Agent Combretastatin A-4." Bioorganic and Medicinal Chemistry Letters 6(2): 157-160.

Berridge M. V., et al., (1996). "The biochemical and cellular basis of cell proliferation assays the use Tetrazolium salts" Biochemica 4: 15-19.

Brown, M. L., et al., (2000). "Comparative Molecular Field Analysis of Colchicine Inhibition and Tubulin Polymerization for Combretastatins Binding to the Colchicine Binding Site on Beta Tubulin." Bioorganic and Medicinal Chemistry 8: 1433-1441.

Chen, Z., et al., (2000). "Preparation of New Anti-Tubulin Ligands through a Dual-Mode, Addition-Elimination Reaction to a Bromo-Substituted □□-Unsaturated Sulfoxide." Journal of Organic Chemistry 65(25): 8811-8815.

Cushman, M., et al., (1992). "Synthesis and Evaluation of Analogues of (Z)-1-(4-methoxyphenyl)-2-(3,4,5-trethane as Potential Cytotoxic and Antimitotic Agents." Journal of Medicinal Chemistry 35(12): 2293-2306.

Dark, et al., (1997). "Combretastatin A4, an Agent that Displays Potent and Selective Toxicity toward Tumor Vasculature." Anticancer Research 57: 1829-1834.

del Rey, B., et al., (1999). "Leishmanicidal Activity of Combretastatin Analogues and Heteroanalogues." Bioorganic and Medicinal Chemistry Letters 9: 2711-2714.

Deshpande, V. H., et al., (1992). "Synthesis of Combretastatin D-2." Tetrahedron Letters 33(29): 4213-4216.

El-Zayet, A. A. E., et al., (1993). "In vitro Evaluation of the Antineoplastic Activity of Combretastatin A-4, a natural product from Combretum caffrum."Anticancer Drugs 4: 19-25.

Galbraith, S. M., et al., (2001). "Effects of Combretastatin A4 Phosphate on Endothelial Cell Morphology In Vitro and Relationship to Tumour Vascular Targeting Activity in Vivo." Anticancer Research 21: 93-102.

Griggs, J., et al., (2001). "Potent Anti-Metastic Activity of Combretastatin-A4." International Journal of Oncology 19: 821-825.

Gwaltney, S. L., et al., (2000). "Novel Sulfonate Analogues of Combretastatin A-4: Potent Antimitotic Agents." Bioorganic and Medicinal Chemistry Letters 11: 871-874.

Hatanaka, T., et al., (1998). "Novel B-ring Modified Combretastatin Analogues: Syntheses and Antineoplastic Activity." Bioorganic and Medicinal Chemistry Letters 8: 3371-3374.

Hori, K., et al., (2001). "Stoppage of Blood Flow in 3-methylcholanthrene-induced Autochthonous Primary Tumor due to a Novel Combretastatin A-4 derivative, AC7700, and its Antitumor Effect." Medical Science Monitor 7(2): 26-33.

Hori, K., et al., (1999). "Antitumor Effects due to Irreversible Stoppage of Tumor Tissue Blood Flow: Evaluation of a Novel Combretastatin A-4 Derivative, AC7700." Jpn. J. Cancer Research 90: 1026-1038.

Iyer, S., et al., (1998). "Induction of Apoptosis in Proliferating Human Endothelial Cells by the Tumor Specific Antiangiogenesis Agent Combretastatin A-4." Cancer Research 58: 4510-4514.

Katsuyoshi, H., et al., (1999). "Antitumor Effects due to Irreversible Storage of Evaluation of a Novel Combretastatin A-4 Derivatives, AC7700." Jpn. J. Cancer Research 90: 1026-1039.

Maya, A. B. S., et al., (2000). "Design, Synthesis, and Cytotoxic Activities of Naphthyl Analogues of Combretastin A-4." Bioorganic and Medicinal Chemistry Letters 10: 2549-2551.

McGown A. T., et al., (1989). "Structural and Biochemical Comparision of the Anti-mitotic Agents Colchicine, Combretastin A-4 and Amphethinile." Anti-cancer Drug Design 3: 249-254.

McGown A. T., et al., (1990). "Differential Cytotoxicity of Combretastatins Al and A4 in Two Daunorubicin-Resident P388 Cell Lines." Cancer Chemotherapy and Pharmacology 26: 79-81.

Medarde, M., et al., (1998). "Synthesis and Antineoplastic Activity of Combretastatin Analogues: Heterocombretastatins." Eur J Nucl Med 33: 71-77.

Medarde, M., et al., (1999). "Synthesis and Pharmacological Activity of Diarylindole Derivatives. Cytotoxic Agents Based on Combretastatins." Bioorganic and Medicinal Chemistry Letters 9: 2303.

Medarde, M., et al., (1995). "Synthesis and Pharmacological Activity of Combretastatin Analogues. Naphthylcombretastatin and Related Compounds." Bioorganic and Medicinal Chemistry Letters 5(3): 229-232.

Nihei, Y, et al., (1999). "A Novel Combretastatin A-4 Derivative AC 7700, Shows Marked Antitumor Activity against Advanced Solid Tumors and Orthotopically Transplant Tumors." Jpn. J. Cancer Research 90: 1016-1025.

Ohsumi, K., et al., (1998). "Syntheses and Antitumor Activity of Cis Restricted Combretastatins: 5 Membered Heterocyclic Analogues." Bioorganic and Medicinal Chemistry Letters 8: 31.53-3158.

Pedley, R. B., et al., (2001). "Eradication of Colorectal Xenografts by Combined Combretastatin A-4 3-0Phosphate." Cancer Research 61: 4716-4722.

Pettit, George R. Combretastatin A-4 Prodrug-Anti-Tumor Chemotherapy. U.S. Pat. No. 5,561,122.

Pettit, George R. Cell Growth Inhibitory Macrocyclic Lactones Denominated Combretastatin D-1 and D-2. U.S. Pat. No. 4,940,726.

Pettit, George R., Sheo B. Singh. Combretastatin A-4Tubulin Polymerization Inhibitor; Antitumor Agent. U.S. Pat. No. 4,996,237.

Pettit, G. R., et a., (1999). "Antineoplastic Agents. 410. Asymmetric Hydroxylation of trans-Combretastatin A-4." Journal of Medicinal Chemistry 42: 1459-1465.

Pettit, G. R., et al., (1998). "Antineoplastic Agents. 379. Synthesis of Phenstatin Phosphate." Journal of Medicinal Chemistry 41: 1688-1695.

Pettit, G. R., et al., (1995). "Antiangioplastic agents 322. Synthesis of combretastiatin A-4 prodrugs." Anticancer Drug Design 10: 299-309.

Pettit, G. R., et al., (1982). "Isolation and Structure of Combretastatin." Canadian Journal of Chemistry 60: 1374-1376.

Pettit, G. R., and John W. Lippert (2000). "Antineoplastic Agents 429. Syntheses of the Combretasatin A-1 and Combretastatin B-1 prodrug." Anti-cancer Drug Design 15: 203-216.

Pettit, G. R., Sheo Bux Singh (1987). "Isolation, Structure, and Synthesis of Combretasatin A-2, A-3, and B-2." Canadian Journal of Chemistry 65: 2390.

Pinney, K. G., et al., (2000). "Synthesis and Biological Evaluation of Aryl Azide Derivatives of Combretastatin A-4 as Molecular Probes for Tubulin." Bioorganic and Medicinal Chemistry 8: 2417-2425.

Rey, B. d., et al., (1999). "Leishmanicidal Activity of Combretastatin Analogues and Heteroanalogues." bioorganic and Medicinal Chemistry Letters 9: 2711-2714.

Russell, G., et al., (1995). "Inhibition of [H] Mebendazole Binding to Tubulin by Structurally Diverse Microtubul Inhibitors which Interact at the Colchicine Binding Site." Biochemistry and Molecular Biology International 35(6): 1153-1159.

Sackett, D. L. (1993). "Podophyllotoxin, Steganacin and Combretastatin: Natural Products1 that Bind at the Colchicine Site of Tubulin." Pharmarc. Ther 59: 163-228.

Schwikkard, S., et al., (2000). "Bioactive Compounds from Combretum erythrophyllum." Journal of Natural Products 63: 457-460.

Sello, G., et al., (1996). "Using a Canonical Matching to Measure the Similarity Between Molecules: The Taxol and the Combretastatin Al Case." Advances in Molecular Similarity 1(243-266).

Shirai, R., et al., (1998). "Asymmetric Synthesis of Antimitotic Combretadioxolane with Potent Antitumor Activity Against Multidrug Resistant Cells." Bioorganic and Medicinal Chemistry Letters 8: 1997-2000.

Shirai, R., et al., (1997). "Synthesis of Conformationary Restricted Combretastatins." Heterocycles 46: 145-148.

Springer Matthew L., et al., (2000). Angiogensis monitored by perfusion with a space-filling microbead suspension. Molecular Therapy 1: 82-87.

Tan, L. P., et al., (1975). "Effects of Indole Alkaloids and Related Compounds on the Properties of Brain Microtubular Protein." Biochem. Sec. Trans. 3(1): 121-124.

Tozer, G. M., et al., (2001). "Mechanisms Associated with Tumor Vascular Shut-Down Induced by Combretastatin A-4 Phosphate: Intravital Microscopy and Measurement of Vascular Permeability." Cancer Research 61: 6413-6422.

Watts, M. E., et al., (1997). "Effects of Novel and Conventional Anti-Cancer Agents on Human Endothelial Permeability: Influence of Tumour Secreted Factors." Anticancer Research 17: 71-76.

Zhao, S., et al., (1999). "Positron Emission Tomography of Murine Liver Metastases and the Effects of Treatment by Combretastatin A-4." Eur J Nucl Med 26: 231-238.

What is claimed is:

[1. A compound of the formula:

(I)

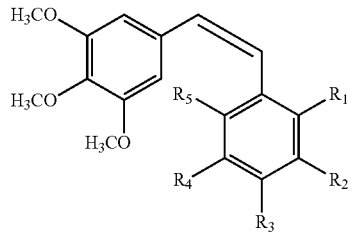

wherein:

$R_1$, $R_4$ and $R_5$ is independently H, OH, lower alkoxy, $NH_2$, $NO_2$, $N_3$, NH—$R_6$, halogen, a phosphate ester salt moiety of the general formula (—O—P(O)$(O^-M^+)_2$ or (—OP(O)$(OR_9)(O^-M^+)$; or —$OPO_3R_7R_8$;

$R_2$ is H, OH, lower alkoxy, $NH_2$, $NO_2$, NH—$R_6$, or phosphate ester salt moiety of the general formula (—O—P(O)$(O^-M^+)_2$ or (—OP(O)$(OR_9)(O^-M^+)$; or —$OPO_3R_7R_8$, wherein $NH_2$ or OH may cyclize with $R_1$;

$R_3$ is H, lower alkoxy, or phosphate ester salt moiety of the general formula (—O—P(O)$(O^-M^+)_2$ or (—OP(O)$(OR_9)(O^-M^+)$; or —$OPO_3R_7R_8$;

$R_6$ is an acylamino group;

$R_7$ is an ammonium salt ($NH_4^+$);

$R_8$ is lower alkyl, cycloalkyl, or aryl;

$R_9$ is an alkyl or branched alkyl substituent, or a benzyl or aryl group; and

M is a metal cation or salt, wherein at least one of $R_1$, $R_2$, $R_3$ $R_4$ or $R_5$ is a phosphate ester salt moiety of the general formula (—OP(O)$(OR_9)(O^-M^-)$.]

[2. The compound of claim 1, wherein:

$R_1$, $R_4$ and $R_5$ are independently H, OH or $NHR_6$;

$R_2$ is H, or a phosphate ester salt moiety of the general formula (—OP(O)$(OR_9)(O^-M^+)_2$, wherein M is a metal cation or salt such as Na, K and Li; or has the formula —$OPO_3R_7R_8$;

$R_3$ is lower alkoxy; and $R_6$ is an acylamino group.]

[3. The compound of claim 1 or 2, wherein said acylamino group is serineamide.]

[4. A pharmaceutical composition comprising the compound of claim 1 as active component, and a pharmaceutically acceptable carrier.]

5. A compound of the formula:

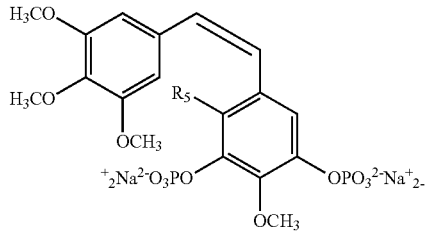

6. A compound of the formula:

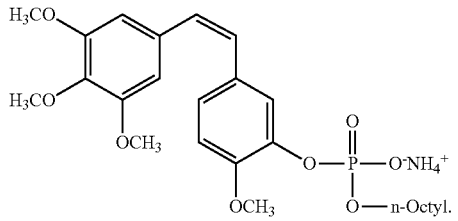

7. A compound of the formula:

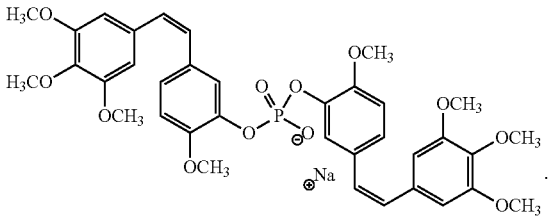

8. A compound of the formula:

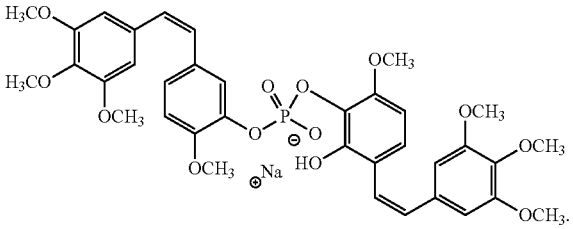

9. A compound of the formula:

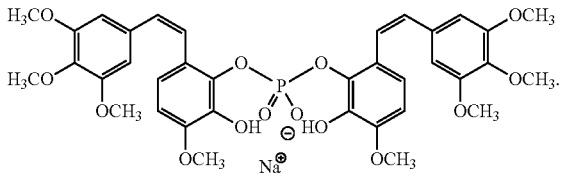

[10. A compound of formula:

(II)

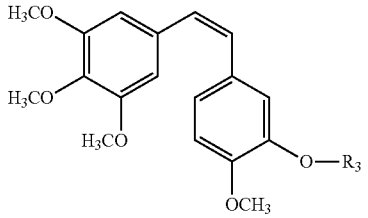

wherein:

$R_1$ is a phosphate ester salt moiety of the general formula ($—P(O)(O^-M^+)_2$), wherein M is a metal cation or salt such as Na, K and Li, $—PO_3R_2R_3—$, or an alkyl sulfonate;

$R_2$ is an alkyl group or an ammonium salt ($NH_4^+$); and $R_3$ is an alkyl group, an aryl group or a cycloalkyl.]

[11. The compound of claim 10, wherein $R_1$ is a phosphate ester salt moiety of the general formula $—PO_3R_2R_3$;

$R_2$ is an ammonium salt ($NH_4^+$); and $R_3$ is an alkyl group.]

[12. A pharmaceutical composition comprising a compound 10 as active component and a pharmaceutically acceptable carrier.]

* * * * *